United States Patent
Yamato et al.

(10) Patent No.: US 9,176,155 B2
(45) Date of Patent: Nov. 3, 2015

(54) SAMPLE PROCESSING APPARATUS

(75) Inventors: Takashi Yamato, Kakogawa (JP);
Hiroshi Kurono, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 438 days.

(21) Appl. No.: 12/883,681

(22) Filed: Sep. 16, 2010

(65) Prior Publication Data

US 2011/0076780 A1   Mar. 31, 2011

(30) Foreign Application Priority Data

Sep. 29, 2009 (JP) .................................. 2009-225605

(51) Int. Cl.
*G01N 35/00* (2006.01)
*G01N 35/02* (2006.01)

(52) U.S. Cl.
CPC ........ *G01N 35/026* (2013.01); *G01N 35/00623* (2013.01); *G01N 2035/00306* (2013.01); *Y10T 436/114165* (2015.01); *Y10T 436/25* (2015.01)

(58) Field of Classification Search
None
See application file for complete search history.

(56) References Cited

U.S. PATENT DOCUMENTS

| 4,609,017 A * | 9/1986 | Coulter et al. ..................... 141/1 |
| 5,735,387 A | 4/1998 | Polaniec et al. |
| 2003/0089581 A1* | 5/2003 | Thompson et al. ........... 198/619 |
| 2009/0220379 A1 | 9/2009 | Wakamiya et al. |

FOREIGN PATENT DOCUMENTS

CN            101520463 A        9/2009

* cited by examiner

*Primary Examiner* — Yelena G Gakh
*Assistant Examiner* — Michelle Adams
(74) *Attorney, Agent, or Firm* — Sughrue Mion, PLLC

(57) ABSTRACT

A sample processing apparatus includes a sample processing unit for obtaining a sample from a sample container and performing a predetermined process of the sample; a transport unit which includes a transport region for transporting, in a transport operation, a sample rack holding the sample container to the sample processing unit, and a rack removal region where the sample rack is accessible to an operator. A restraining member is also provided, which restrains contact by the operator to the sample rack on the transport region. A transport controller controls the transport unit to transport the sample rack on the transport region to the rack removal region after a predetermined transport suspension event occurs during the transport operation.

16 Claims, 29 Drawing Sheets

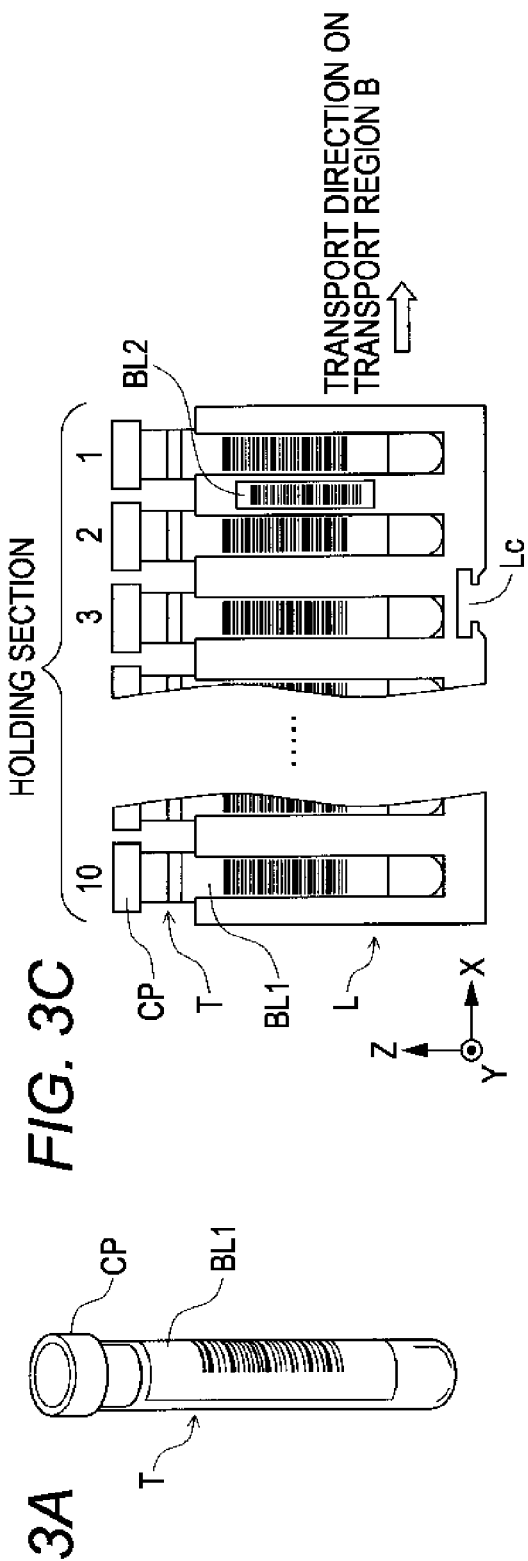
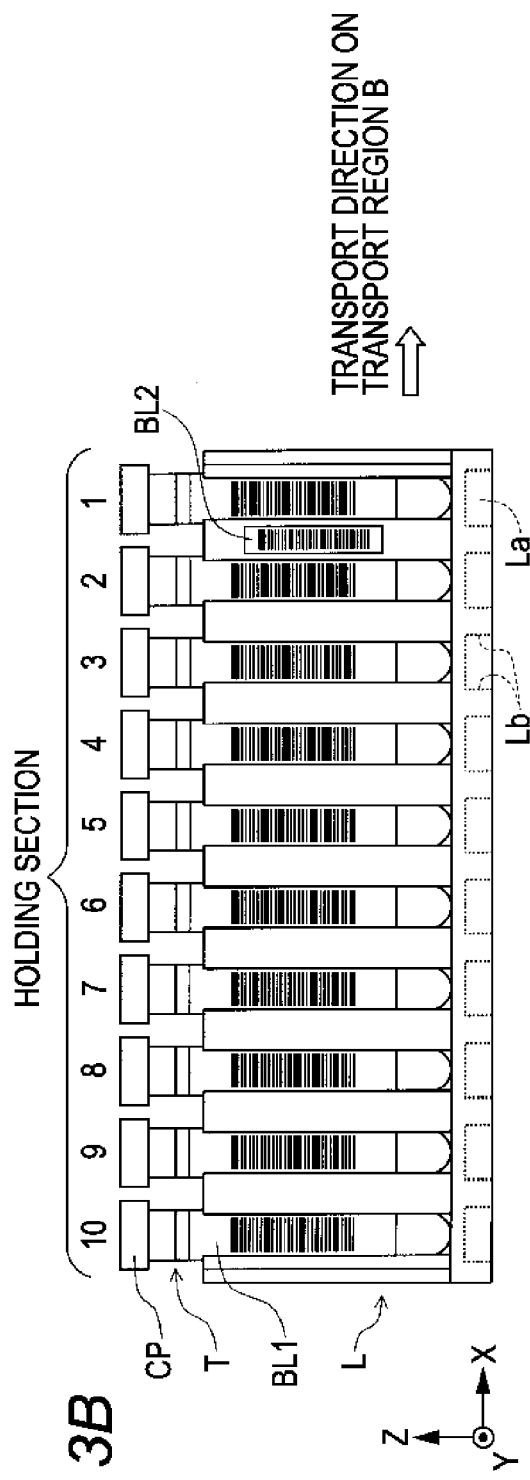

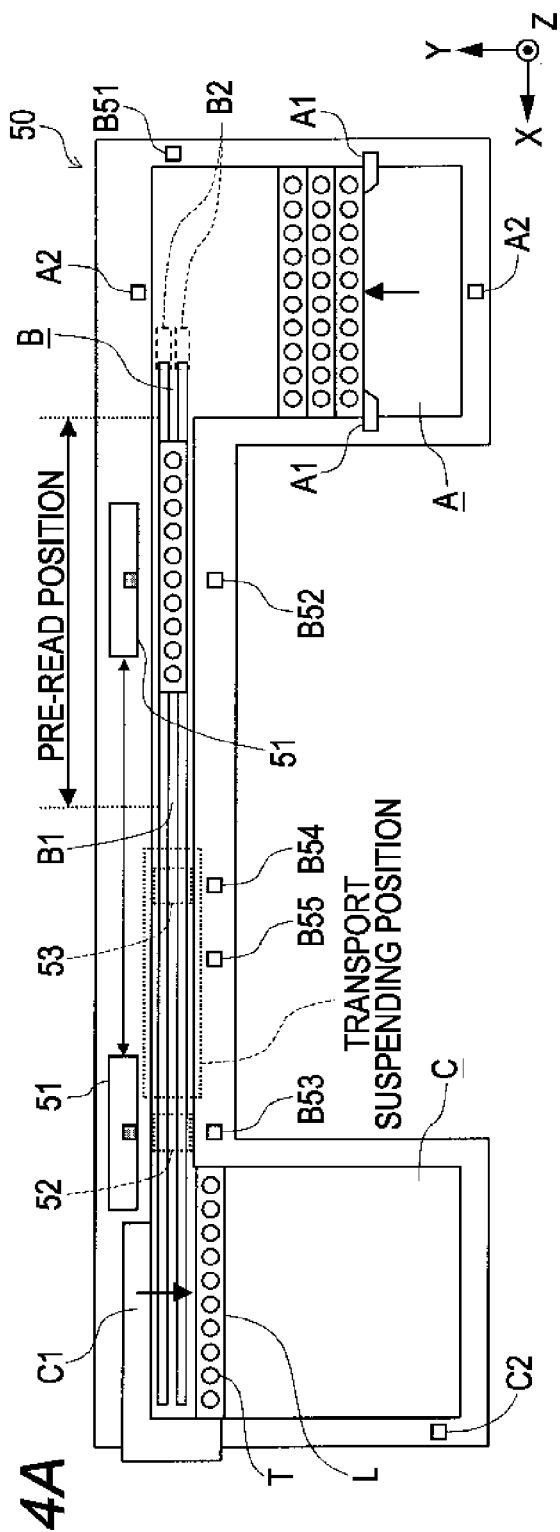
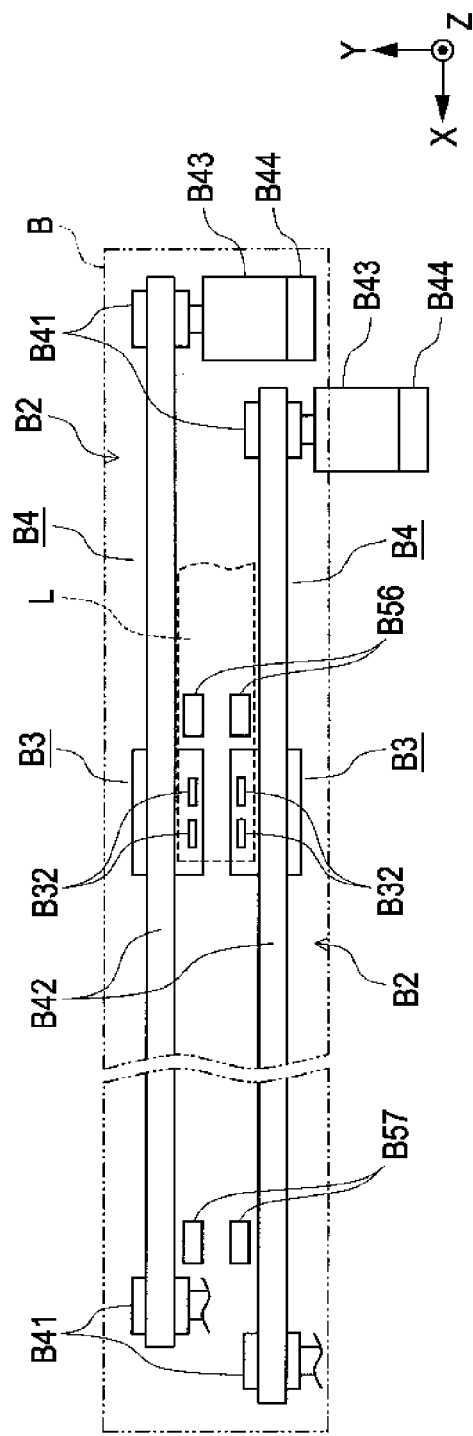
FIG. 4A
FIG. 4B

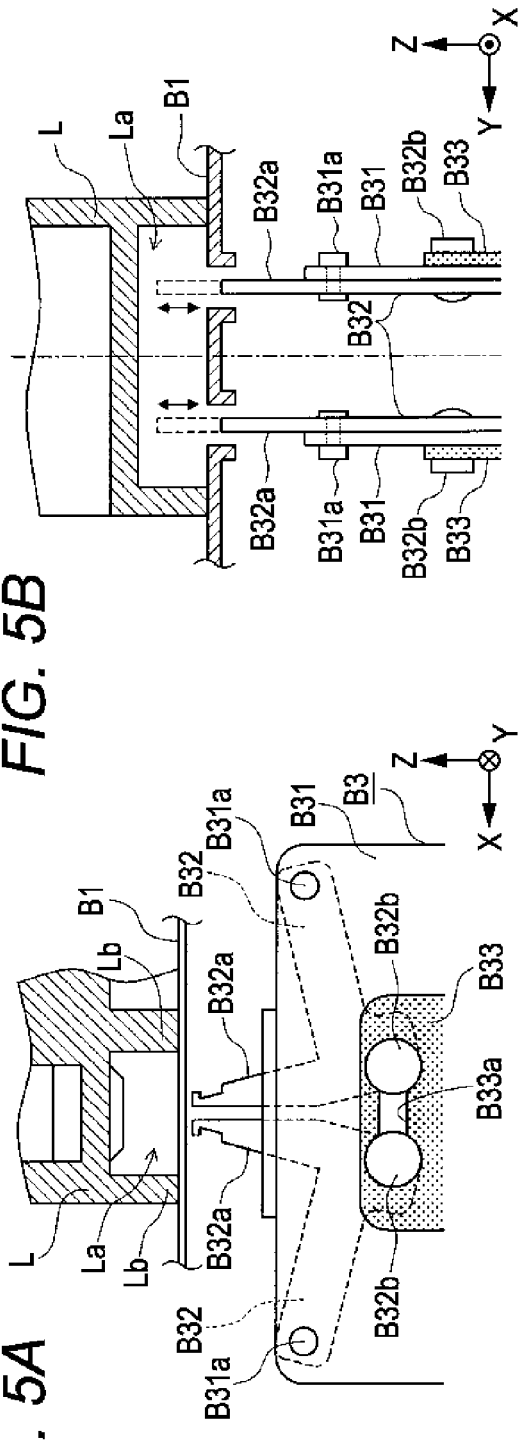
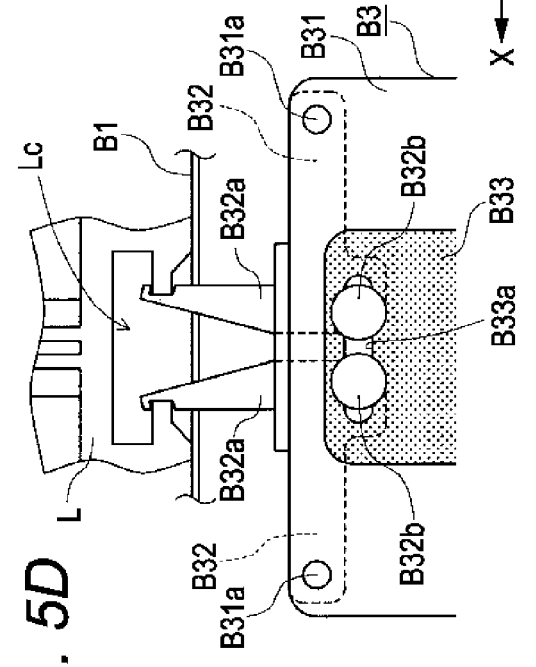
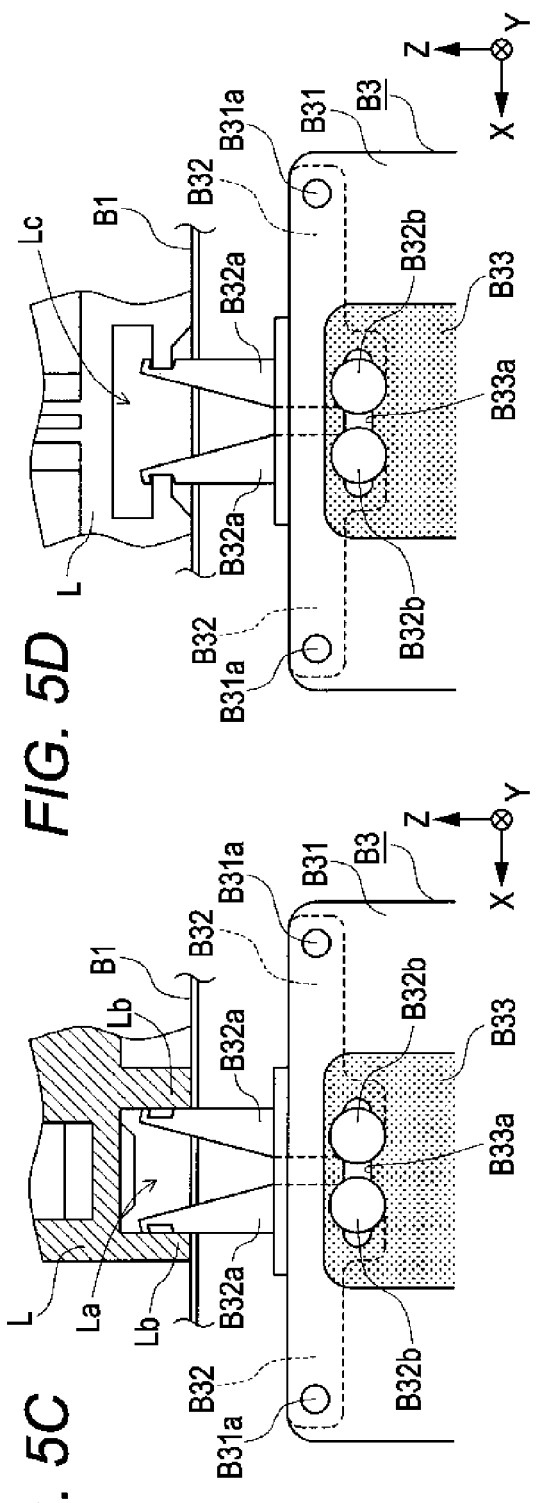

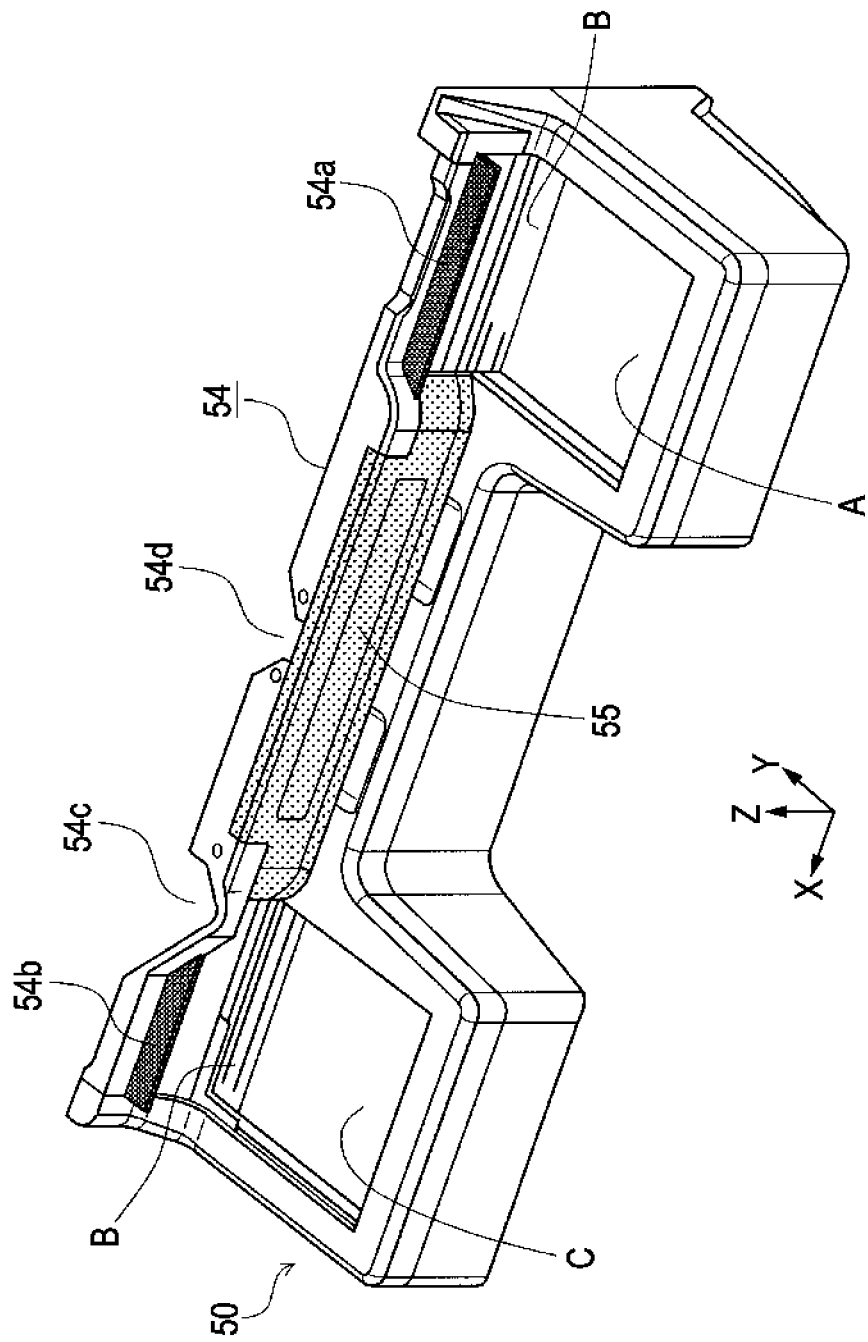

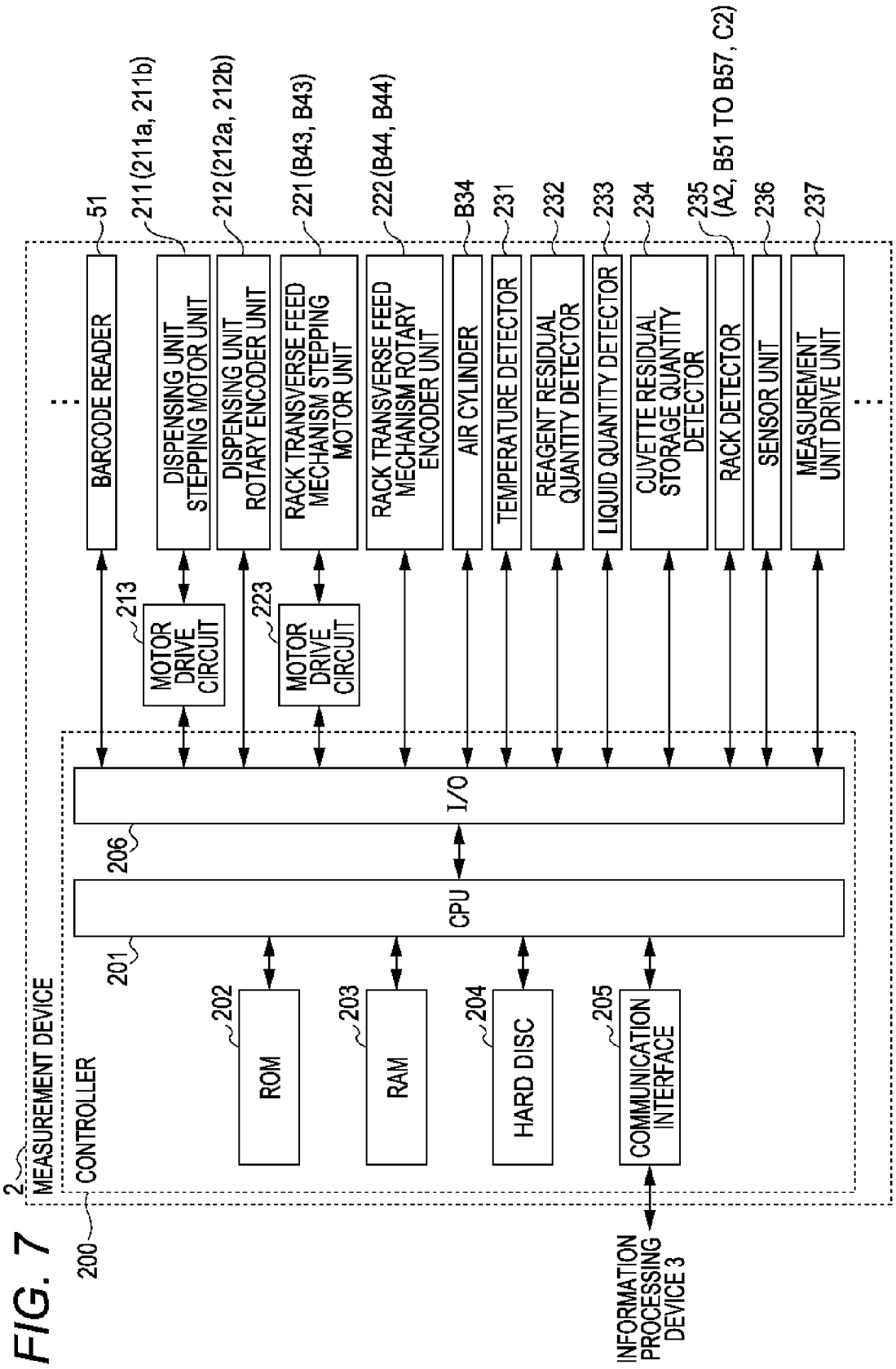

FIG. 14A

| RACK POSITION | HOLDING POSITION | SAMPLE BARCODE READ STATUS | MEASUREMENT MODE | SUCTIONING STATUS |
|---|---|---|---|---|
| SAMPLE SUCTIONING POSITION | 1 | FINISHED | STANDARD | FINISHED |
| | 2 | FINISHED | STANDARD | FINISHED |
| | 3 | FINISHED | STANDARD | FINISHED |
| | 4 | FINISHED | STANDARD | FINISHED |
| | 5 | FINISHED | TRACE LEVEL | FINISHED |
| | 6 | FINISHED | TRACE LEVEL | UNFINISHED |
| | 7 | FINISHED | STANDARD | UNFINISHED |
| | 8 | FINISHED | STANDARD | UNFINISHED |
| | 9 | FINISHED | STANDARD | UNFINISHED |
| | 10 | FINISHED | STANDARD | UNFINISHED |

FIG. 14B

| RACK POSITION | HOLDING POSITION | SAMPLE BARCODE READ STATUS | MEASUREMENT MODE | SUCTIONING STATUS |
|---|---|---|---|---|
| PRE-READ POSITION | 1 | FINISHED | STANDARD | UNFINISHED |
| | 2 | FINISHED | STANDARD | UNFINISHED |
| | 3 | FINISHED | STANDARD | UNFINISHED |
| | 4 | FINISHED | TRACE LEVEL | UNFINISHED |
| | 5 | FINISHED | TRACE LEVEL | UNFINISHED |
| | 6 | UNFINISHED | STANDARD | UNFINISHED |
| | 7 | UNFINISHED | TRACE LEVEL | UNFINISHED |
| | 8 | UNFINISHED | TRACE LEVEL | UNFINISHED |
| | 9 | UNFINISHED | STANDARD | UNFINISHED |
| | 10 | UNFINISHED | TRACE LEVEL | UNFINISHED |

FIG. 15

| STATE | RACK NUMBER-POSITION | SAMPLE NUMBER | MEASUREMENT MODE | DATE | TIME | PT% |
|---|---|---|---|---|---|---|
| ... | ... | ... | ... | ... | ... | ... |
| | 000001-01 | 1* | N | 2009/01/05 | 13:15 | 121.3 |
| | 000001-01 | 1* | N | 2009/01/05 | 16:59 | 121.3 |
| | 000001-02 | 2* | N | 2009/01/05 | 16:59 | 102.9 |
| | 000001-03 | 3* | M | 2009/01/05 | 17:00 | 64.1 |
| | 000001-04 | 4* | M | 2009/01/05 | 17:00 | 118.8 |
| | 000001-05 | 5* | N | 2009/01/05 | 17:00 | 48.0 |
| | 000001-01 | 1* | N | 2009/01/05 | 17:07 | 10.7 |
| | 000001-02 | 2* | N | 2009/01/05 | 17:07 | 10.5 |
| ERROR | 000001-03 | 3* | N | | | ****.* |
| ERROR | 000001-04 | 4* | N | | | ****.* |

SAMPLE PROCESSING APPARATUS

CROSS REFERENCE TO RELATED APPLICATION

This application claims priority from Japanese Patent Application No. 2009-225605, filed on Sep. 29, 2009, in the Japanese Patent Office.

FIELD OF THE INVENTION

The present invention relates to a sample processing apparatus for processing a sample such as blood or urine, and a sample rack transporting method.

BACKGROUND

U.S. Pat. No. 5,735,387 discloses a sample processing apparatus for suctioning a sample from a sample container retained in a sample rack and processing the suctioned sample. This conventional sample processing apparatus is provided with a transport unit for transporting a sample rack holding sample containers to a sample suctioning position. The transport unit has an input region, a process region, and an output region, wherein a sample rack having a structure capable of holding a plurality of sample containers is set in the input region. The sample rack set in the input region is transported toward the suctioning position in front of a sample processing unit to enter the process region. Then, a sample of the sample container retained in the sample rack is suctioned at the sample suctioning position on the process region. The sample rack stays on the process region until a processing result is obtained by the sample processing unit. After the processing result is obtained from all of the sample containers retained in the sample rack, the sample rack is transported from the process region to the output region.

In this sample processing apparatus, the process region is encompassed by a protective housing to prevent a user from easily accessing the sample container after the sample container is transported from the input region to the process region. According to such a structure, once the sample containers are placed in the process region, the user is unable to change the arrangement and positional order of the sample containers.

In the case where a certain transport suspension event occurs during the sample processing operation, the above sample processing apparatus stops the processing operation by the sample processing unit and the transport operation by the transport unit. In this case, the processing operation by the sample processing unit and the transport operation by the transport unit restart after the suspension event is resolved. When restarting the operations, the user may have to return the sample rack currently on a transport path to the input region.

However, when the process region is covered with the protective housing as described above, the user cannot easily access the sample rack placed in the process region. Thus, it is difficult to obtain the sample rack in the case where the sample rack is located in the process region when the transport operation by the transport unit is suspended. This causes a problem in that the user has to go through some time-consuming steps to remove the sample rack from the process region.

SUMMARY

The scope of the present invention is defined solely by the appended claims, and is not affected to any degree by the statements within this summary.

A first aspect of the present invention is a sample processing apparatus, comprising: a sample processing unit for obtaining a sample from a sample container and performing a predetermined process of the sample; a transport unit which includes a transport region for transporting, in a transport operation, a sample rack holding the sample container to the sample processing unit, a rack removal region where the sample rack is accessible to an operator, and a restraining member for restraining contact by the operator to the sample rack on the transport region; and a transport controller for controlling the transport unit to transport the sample rack on the transport region to the rack removal region after a predetermined transport suspension event occurs during the transport operation.

A second aspect of the present invention is a sample processing apparatus, comprising: a sample processing unit for obtaining a sample from a sample container and performing a predetermined process of the sample; a transport unit for transporting, in a transport operation, the sample rack holding the sample container to the sample processing unit; and a transport controller for controlling the transport unit in accordance with a type of transport suspension event after the transport suspension event occurs during the transport operation.

A third aspect of the present invention is a sample rack transporting method, comprising: in a transport operation, transporting a sample rack holding a sample container, by a transport unit, to a sample processing unit for processing a sample in the sample container; and controlling the transport unit to transport the sample rack to a rack removal region where an operator has access to the sample rack after a predetermined transport suspension event occurs during the transport operation in a restraining region where the operator is restrained from contacting the sample rack.

A fourth aspect of the present invention is a sample processing apparatus, comprising: a transport unit configured to transport a plurality of samples in racks holding sample containers to a sample processing unit in a transport region, and configured to transport the racks to a rack removal region where at least the sample containers are accessible to an operator, a restraining member configured to prevent the operator from contacting at least the sample containers in at least a portion of the transport region; and a processor electronically controlling the transport unit to transport at least given ones of the racks in the transport region to the rack removal region in response to a signal indicating a predetermined transport suspension event.

A fifth aspect of the present invention is an apparatus, comprising: a transport unit configured to transport, in a transport operation, a sample rack holding a sample in a sample container in a transport region to a sample processing unit configured to perform a predetermined process of the sample, wherein the transport unit is further configured to remove the sample rack from the transport region; and a processor configured to detect a plurality of transport suspension events and to electronically control the transport unit, in the transport operation, to remove the sample rack from the transport region in accordance with detection of at least one of the transport suspension events.

BRIEF DESCRIPTION OF THE DRAWINGS

FIGS. 3A to 3C are diagrams of a sample container and a sample rack according to the embodiment;

FIGS. 4A and 4B are plan views illustrating a structure of a transport unit according to the embodiment;

FIGS. 5A to 5D are schematic diagrams of principal parts of an engagement unit according to the embodiment;

FIG. 6 is a perspective view of the transport unit according to the embodiment;

FIG. 7 is a diagram illustrating a circuit configuration of the measurement device according to the embodiment;

FIGS. 14A and 14B illustrate a transport operation control list of a preceding rack and a transport operation control list of a subsequent rack according to the embodiment;

FIG. 15 illustrates a job list according to the embodiment;

DETAILED DESCRIPTION OF THE EMBODIMENT

Hereinafter, a sample processing apparatus according to an embodiment is described with reference to the accompanied drawings. The embodiment described below is only illustrated as an example of embodying the present invention. The present invention is by no means limited to the embodiment described below.

Figure 1:
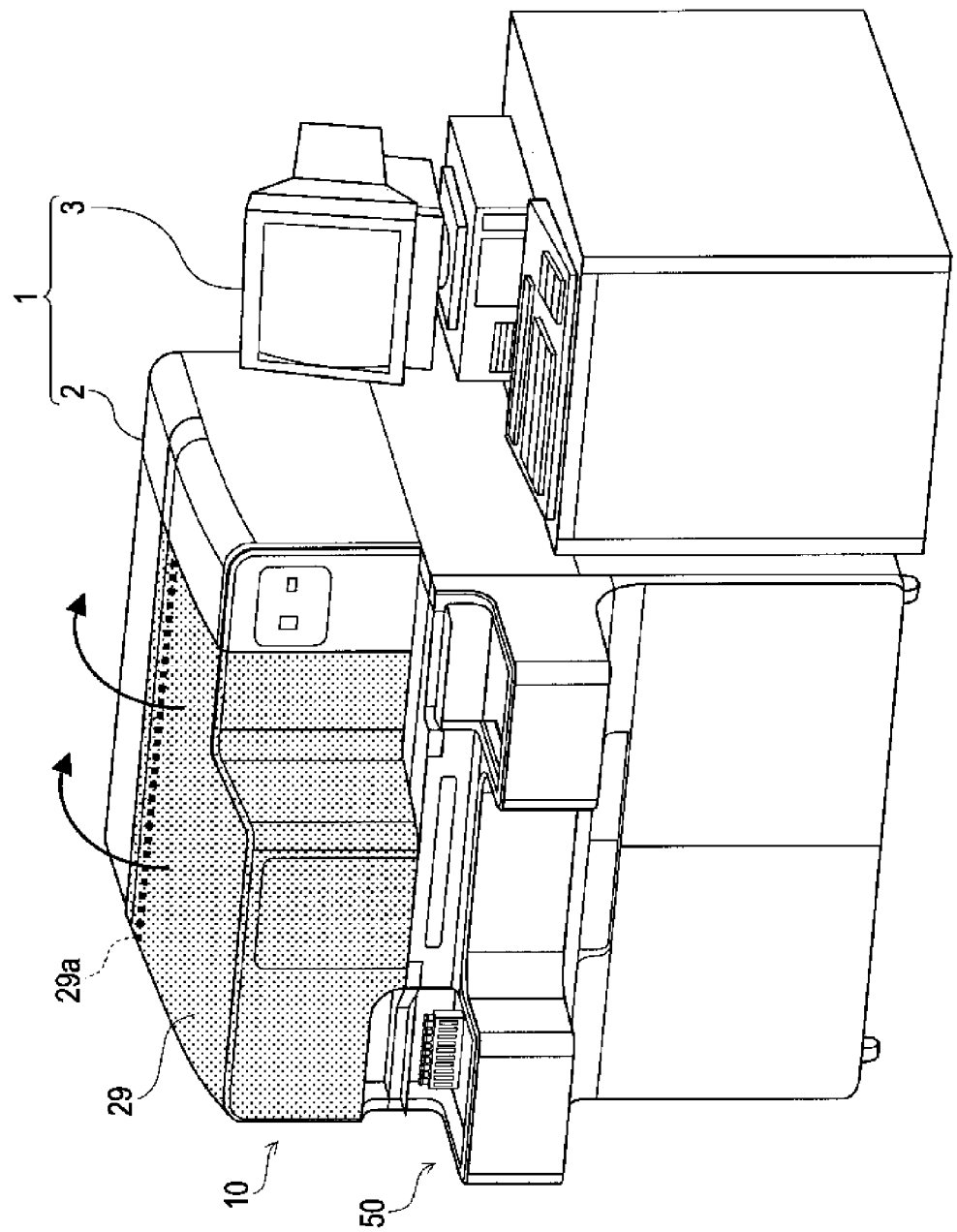
FIG. 1 illustrates a structure of a sample processing apparatus according to an embodiment.

FIG. 1 is a diagram illustrating a structure of a sample processing apparatus 1 according to the present embodiment. The sample processing apparatus 1 is a blood coagulation analyzing apparatus for optically measuring and analyzing a sample by irradiating with light a measurement specimen prepared by adding a reagent to the sample (plasma) by employing techniques of solidification, synthetic substrate, immunonephelometry, and agglutination. The sample processing apparatus 1 has a measurement device 2 which optically measures components included in the sample (plasma), and an information processing device 3 which analyzes measurement data obtained by the measurement device 2 and transmits operation commands to the measurement device 2.

The measurement device 2 is provided with a main body cover 29 as illustrated in the figure. As the main body cover 29 rotates on a rotational shaft 29a as illustrated in the figure, a measurement unit 10 described later can be opened or closed.

Figure 2:
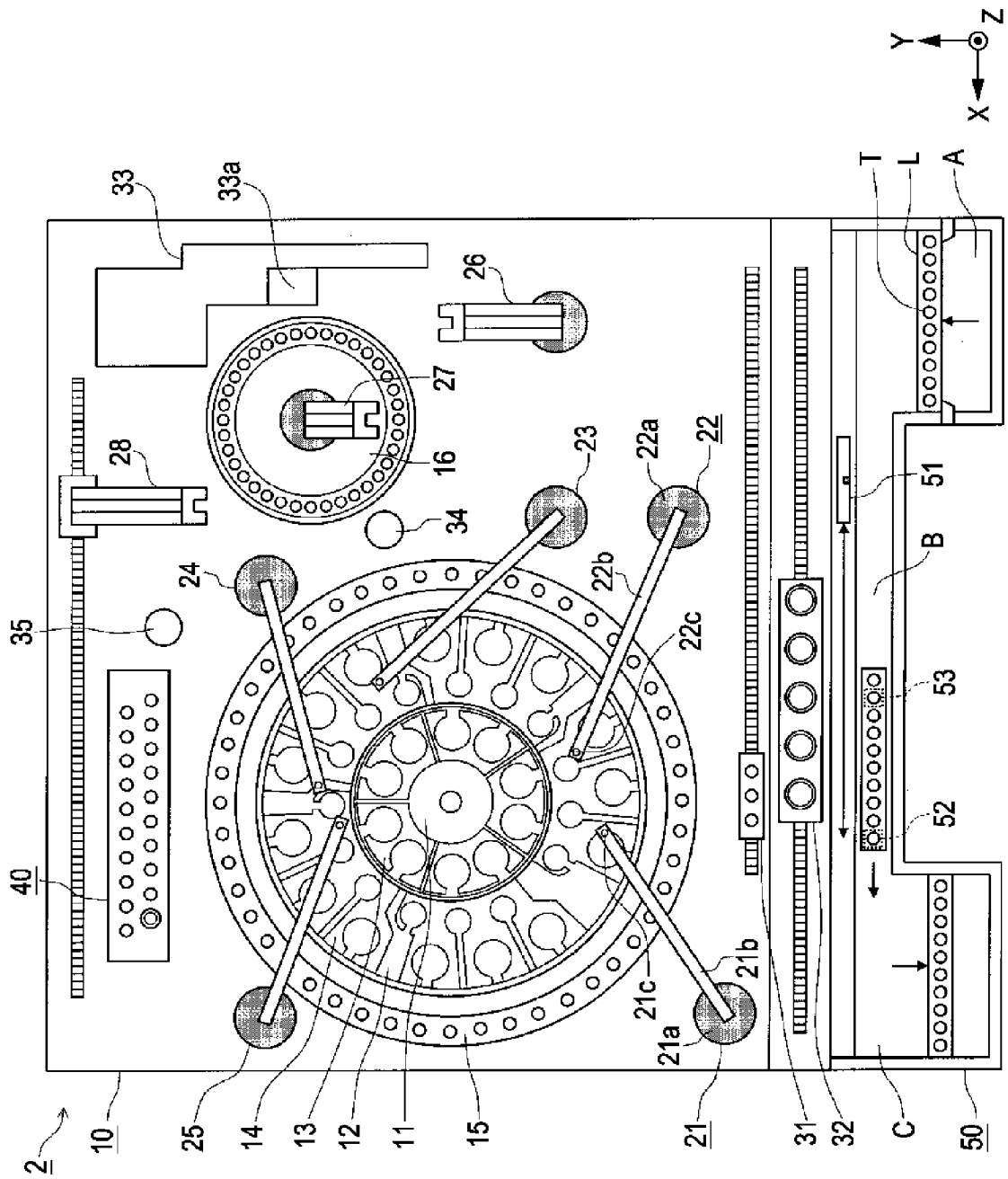
FIG. 2 is a plan view schematically illustrating an internal structure of a measurement device according to the embodiment.

FIG. 2 is a plan view schematically illustrating an internal structure of the measurement device 2 when viewed from an upper direction. The measurement device 2 includes the measurement unit 10, a detection unit 40, and a transport unit 50.

As illustrated in the figure, the transport unit 50 is provided with a rack set region A where a sample rack L can be disposed, a transport region B, and a rack placement region C. The sample rack L has holding sections so that a plurality of sample containers T can be held therein. The sample container T contains therein a sample to be measured.

The sample rack L set in the rack set region A is transported rearward along the rack set region A (Y-axis positive direction) to reach the right end of the transport region B (end in X-axis negative direction). The sample rack L positioned at the right end of the transport region B is then transported leftward (X-axis positive direction) along the transport region B.

As illustrated in the figure, a barcode reader 51, which is movable rightward and leftward (X-axis negative and positive directions), is provided in the transport region B. The barcode reader 51 reads barcode labels respectively affixed to the sample container T and the sample rack L at a predetermined position on the transport region B. Sample suctioning positions 52 and 53 are set at predetermined positions of the transport region B.

When the sample containers T are positioned at the sample suctioning positions 52 and 53, the samples contained in the sample containers T at the positions are respectively suctioned by sample dispensing units 21 and 22 described later. After all of the samples in the sample containers T held in the sample rack L are suctioned, the sample rack L is transported to the left end of the transport region B.

In the sample processing apparatus 1 according to the present embodiment, a measurement mode from two different measurement modes; "standard measurement" and "trace-level measurement" can be selected. In the standard measurement, the sample of the sample container T is suctioned by the sample dispensing unit 21 at the sample suctioning position 52. In the trace-level measurement, the sample of the sample container T is suctioned by the sample dispensing unit 22 at the sample suctioning position 53.

The sample rack L positioned at the left end of the transport region B is transported forward along the rack placement region C (Y-axis negative direction), where the transport operation of the sample rack L ends. The transport operation by the transport unit 50 is consecutively carried out for all of the sample racks L set in the rack set region A.

The sample dispensing unit 21 includes a support member 21a, an arm 21b supported by the support member 21a, and a pipette 21c attached to a tip of the arm 21b. The support member 21a is rotated by a stepping motor 211a provided on a rear side of a lower surface (see FIG. 7), and the arm 21b is driven upward and downward by the stepping motor 211a (Z-axis positive and negative directions). The pipette 21c is used to suction and discharge the sample. When the support member 21a is rotated, the pipette 21c moves on an outer periphery of a circle centered on the support member 21a.

The sample dispensing unit 22 has a structure similar to that of the sample dispensing unit 21. More specifically, the sample dispensing unit 22 includes a support member 22a, an arm 22b, and a pipette 22c attached to a tip of the arm 22b. The support member 22a is rotated by a stepping motor 211b provided on the lower-surface rear side (see FIG. 7), and the arm 22b is driven upward and downward by the stepping motor 211b. The pipette 22c is used to suction and discharge the sample.

To suction the samples, to start with, the sample dispensing units 21 and 22 respectively rotate the support members 21a and 22a to position the pipettes 21c and 22c at the sample suctioning positions 52 and 53. When the arms 21b and 22b are thereafter driven downward, the pipettes 21c and 22c are inserted into the sample containers T. After the samples are suctioned, the arms 21b and 22b are driven upward so that the pipettes 21c and 22c are drawn out of the sample containers T.

The samples suctioned at the sample suctioning positions 52 and 53 are put in cuvettes of a cuvette carrier 31 directly or by way of cuvettes of a cuvette table 15. At this time, a suitable volume of diluent set in a diluent carrier 32 is suctioned by the sample dispensing unit 22 to be mixed with the samples of the cuvettes. Then, the cuvette carrier 31 is driven rightward (X-axis negative direction) so that the cuvettes are transported to the front of a catcher unit 26. The cuvettes set in the cuvette carrier 31 are held by the catcher unit 26 and then set in a warming table 16. Then, the cuvettes are transported by catcher units 27 and 28 to be set in the detection unit 40. At this time, a suitable volume of reagents retained in reagent tables 11 and 12 are injected into the cuvettes by reagent dispensing units 23, 24 and 25. Then, the detection unit 40 processes the contents of the cuvettes to detect optical information which reflects thereon components included in the measurement specimens in the cuvettes.

A cuvette supply unit 33 can sequentially supply a plurality of cuvettes thus obtained to a cuvette storage 33a. The cuvettes newly supplied to the cuvette storage 33a are set in retaining holes of the cuvette table 15 and the cuvette carrier 31 by the catcher units 26 and 27, respectively. The post-analysis cuvettes to be discarded are thrown into waste vents 34 and 35 by the catcher units 27 and 28. The sample dispensing units 21 and 22, and the pipettes of the reagent dispensing unit 23 to 25 are washed at a predetermined washing position (not illustrated). A washing solution which was used for washing is kept in a waste solution tank (not illustrated).

On the reagent tables 11 and 12, container racks 13 and 14 are respectively disposed. The container racks 13 and 14 respectively hold therein a plurality of reagent containers in which reagents are contained. To exchange the reagents contained in the reagent container, the main body cover 29 illustrated in FIG. 1 is opened after the measuring operation by the measurement unit 10 is suspended. Then, an operator can retrieve the reagent containers from the reagent tables 11 and 12 to replace the reagents with new ones.

FIG. 3A is a perspective view illustrating an external appearance of the sample container T, and FIGS. 3B and 3C are front views of the sample rack L. FIG. 3B and FIG. 3C are front views of the sample rack L when the sample rack L set in the transport unit 50 is viewed in the Y-axis negative direction illustrated in FIG. 2.

Referring to FIG. 3A, the sample container T is a tubular container made of optically transparent glass or synthetic resin, wherein an upper end is open. A blood sample collected from a patient is contained therein, and the opening at the upper end thereof is sealed with a cap portion CP. A barcode label BL1 is affixed to a side surface of the sample container T. The barcode label BL1 has a barcode representing a sample ID printed thereon.

Referring to FIG. 3B, the sample rack L has 10 holding sections which can hold 10 sample containers T perpendicularly (upright position). The holding sections respectively have serial numbers 1 to 10 from right which represent their holding positions. A barcode label BL2 is affixed to a side surface of the sample rack L in the Y-axis positive direction. The barcode label BL2 has a barcode representing a rack ID printed thereon.

As illustrated in FIG. 3B, recesses La as many as the holding sections, that is, 10 recesses open downward are formed in a bottom surface of the sample rack L along the longitudinal direction of the sample rack L. The recesses La are each defined by wall portions Lb formed on right and left sides thereof.

The sample rack may have a structure as illustrated in FIG. 3C. In this case, a bottom surface of the sample rack L is provided with one recess Lc.

FIG. 4A is a plan view illustrating a structure of the transport unit 50.

The rack set region A is equipped with a rack feed mechanism A1 which transports the sample rack L disposed therein in the Y-axis positive direction. The rack feed mechanism A1 pushes the side surface of the sample rack L in the rack set region A closer thereto (in Y-axis negative direction) to transport the sample rack L in the Y-axis positive direction so that the sample rack L is transferred to the transport region B. In the event that a plurality of sample racks L are disposed in the rack set region A, as illustrated in the figure, the rack feed mechanism A similarly pushes the side surface of the sample rack L which is nearest thereto (in Y-axis negative direction) so that the sample rack L which is farthest thereto (in Y-axis positive direction) is transferred to the transport region B.

In the rack set region A, as illustrated in the figure, a pair of sensors A2 are provided at an end thereof in the Y-axis positive direction and an end thereof in the Y-axis negative direction. An optically transparent photosensor or the like constitutes the sensor A2. The sensor A2 blocks light when the sample rack L is present in the rack set region A, and transmits light when there is no sample rack L in the rack set region A.

The transport region B is provided with a transport path B1 which supports the bottom surface of the sample rack L, and two rack transverse feed mechanisms B2. The two rack transverse feed mechanisms B2 are provided below the transport path B1, and independently move two sample racks L disposed on the transport path B1 rightward and leftward (X-axis positive and negative directions). A structure of the rack transverse feed mechanism B2 will be described later with reference to FIG. 4B and FIG. 5.

In the sample rack L transferred to the transport region B, the barcode reader 51 reads the barcode BL1 of the sample container T and the barcode label BL2 of the sample rack L (hereinafter, referred to as "pre-read") before the sample container T is transported to the sample suctioning position 52, 53. As illustrated in the figure, the pre-read by the barcode reader 51 is performed when the sample rack L is in the range of "a pre-read position" on the transport region B.

As illustrated in FIG. 2, the sample suctioning positions 52 and 53 are set in the transport region B. The sample rack L for which the pre-read was performed is transported leftward (X-axis positive direction) so that the sample containers T retained in the sample rack L is positioned at the sample suctioning position 52 or 53. The barcode label BL1 of the sample container T positioned at the sample suctioning position 52 or 53 is read by the barcode reader 51 (hereinafter, referred to as "post-read"), and the sample contained therein is then suctioned.

In the case where a first suspension event, which will be described later, occurs during the sample suctioning by the sample dispensing unit 21, 22, the sample rack L is transported to a "transport suspending position", and the transport of the sample rack L stops at the position.

As illustrated in the figure, sensors B51 to B55 are provided in the transport region B. A reflective photosensor or the like constitutes each of the sensors B51 to B55. The sensor B51 detects the sample rack L positioned at the right end of the transport region B (end in the X-axis negative direction). The sensor B52 detects that the sample rack L has been transported to the pre-read position. The sensors B53 and B54 detect that the sample rack L is positioned at the sample suctioning position 52, 53. The sensor B55 detects that the sample rack L has been transported to the transport suspending position.

The rack placement region C is provided with a rack feed mechanism C1 which transports the sample rack L disposed therein in the Y-axis negative direction. The rack feed mechanism C1 moves the sample rack L disposed at the left end of the transport region B (end in the X-axis positive direction) in the Y-axis negative direction by one pitch (equal to width of the sample rack L in its lateral direction) so that the sample rack L is transferred from the transport region B to the rack placement region C.

As illustrated in the figure, the rack placement region C is equipped with a sensor C2 which detects the presence or absence of the sample rack L. A reflective photosensor or the like constitutes the sensor C2. The sensor C2 detects the sample rack L which has been transported to a transport end position (end in the Y-axis negative direction) of the rack placement region C.

FIG. 4B is a plan view illustrating a structure of the rack transverse feed mechanism B2. The two rack transverse feed mechanisms B2 are provided next to each other in the Y-axis direction. The rack transverse feed mechanism B2 is equipped with an engagement unit B3 that can be engaged with the sample rack L, and a movement mechanism B4 which moves the engagement unit B3 rightward and leftward (X-axis positive and negative directions).

The movement mechanism B4 has a pair of pulleys B41 provided at both ends of the transport region B, a belt 42 that bridges the pulleys B41, a stepping motor B43 which rotates one of the pulleys B41, and a rotary encoder B44 which detects number of rotations of the stepping motor B43.

The engagement unit B3 is coupled with the belt B42 of the movement mechanism B4 to move rightward and leftward when the stepping motor B43 is driven. An amount of the movement of the engagement unit B3 is detected by the rotary encoder B44 as the number of rotations of the stepping motor B43. The operation of the stepping motor B43 is controlled based on a detection result obtained by the rotary encoder B44. A movement start position and a movement end position of the engagement unit B3 are respectively set at a right end (end in X-axis negative direction) and a left end (end in X-axis positive direction) in a drivable range of the engagement unit B3. Further, sensors B55 and B56 each including an optically transparent photosensor or the like are provided. The sensors B55 and B56 respectively detect the engagement unit B3 positioned at the movement start position and the movement end position.

FIG. 5A is a front view of the engagement units B3 illustrating a state where the engagement units B3 are not engaged with the sample rack L. FIG. 5B is a side view of the engagement units B3. FIGS. 5C and 5D are front views of the engagement units B3 illustrating a state where the engagement units B3 are engaged with the sample rack L.

Referring to FIG. 5A, the engagement unit B3 has a substrate B31, a pair of engagement members B32, and an action member B33. The engagement unit B3 further has an air cylinder B34 (not illustrated), which moves the action member B33 upward and downward (see FIG. 7).

A guide member (not illustrated) is attached to the substrate B31. The guide member is slidably engaged with a guide rail (not illustrated) along the X-axis direction below the transport path B1. The substrate B31 is supported by the guide rail so as to freely move in the X-axis positive and negative directions.

As illustrated in the figure, the pair of engagement members B32 are secured to an upper side of the substrate B31 by securing tools B31a including bolts and screw nuts so as to freely rotate in the Y-axis direction. Engagement claws B32a are formed at an upper section of the engagement member B32, and engagement rollers B32b are provided at a lower end thereof. The substrate B31 has regulating holes (not illustrated) formed therein each regulating a rotational range of the engagement roller B32b along a rotational line of the engagement roller B32b when the engagement member B32 rotates on the securing tool B31a as a rotational center. The engagement roller 32b is movably engaged with the regulating hole. Accordingly, the engagement member B32 can be rotated in the Y-axis direction within a predetermined range with the securing tool B31a as a rotational center.

A rectangular engagement hole B33a having a larger dimension in its lateral direction is formed at an upper section of the action member B33 so that the pair of engagement rollers B32b are engaged therewith. When the action member B33 is driven in the Z-axis direction, the pair of engagement members B32 respectively rotate on the securing tools B31a in the Y-axis direction via the engagement rollers 32b engaged with the engagement hole B33a. As illustrated in FIG. 5A, in a state where the pair of engagement members B32b rotate downward (Z-axis negative direction), the engagement claws B32a are positioned below the transport path B1, and does not engage with the sample rack L.

The air cylinder B34 is supplied with compressed air from a compressor (not illustrated). The air cylinder B34 has a rod which generates an up-and-down movement as the compressed air is supplied. The action member B33 is fixed to an upper end of the rod of the air cylinder B34. As the rod of the air cylinder B34 moves upward and downward, the action member B33 simultaneously moves upward and downward. In conjunction therewith, the pair of engagement members B32 rotate upward and downward.

Referring to FIG. 5B, as described above, a state where the engagement claws B32a stick out beyond the transport path B1 through grooves formed therein, and a state where the engagement claws B32a stay below the transport path B1 occur in turns as the engagement members B32 rotate, as illustrated in the figure.

Referring to FIG. 5C, when the engagement member B32 rotates upward (Z-axis positive direction), the engagement claws B32a stick out beyond the transport path B1 to advance into the recess La formed in the bottom section of the sample rack L. As a result, the pair of engagement claws B32a are moved away from each other. Accordingly, the engagement claws B32a abut with the wall portions Lb on both sides of the recess La in the X-axis positive and negative directions as illustrated in the figure. Accordingly, the pair of engagement members B32 are finally engaged with the sample rack so that the sample rack L can be securely transported.

Referring to FIG. 5D, in the case where the sample rack L illustrated in FIG. 3C is used, the engagement claws B32a similarly stick out beyond the transport path B1 to advance into the recess Lc formed in the bottom section of the sample rack L so that the pair of engagement claws B32a are moved away from each other. In this case, the engagement claws B32a are engaged with protruding wall portions formed in the recess Lc as illustrated in the figure. Accordingly, the sample rack L illustrated in FIG. 3C can be transported in the same manner as the sample rack L illustrated in FIG. 3B.

The engagement units B3 each having the structure described so far are disposed facing each other in the Y-axis direction below the transport path B1 as illustrated in FIG. 4B, so that two sample racks L is independently driven in the transport region B.

According to the rack transverse feed mechanism B2 structured as above, the sample rack L is transported on the transport path B1 with the recess La in the bottom surface thereof remaining supported by the engagement claws B32a. In the case where the first suspension event described later occurs, the transport of the sample rack L stops on the transport path B, in which case the recess La in the bottom surface of the sample rack L still remains supported by the engagement claws B32a. Even after the sample rack L is stopped, the stepping motor B43 is continuously excited, which prevents the sample rack L from positional shifting.

FIG. 6 is a perspective view of the transport unit 50.

A roof 54 is provided at an upper section near the center of the transport region B (Z-axis positive direction). At the right end of the roof 54 (end in the X-axis negative direction) and the left end of the roof 54 (end in the X-axis positive direction), flange portions 54a and 54b are respectively formed as illustrated. Further, openings 54c and 54d are formed in the roof 54 as illustrated. The sample dispensing units 21 and 22 respectively suction the samples of the sample containers T positioned at the sample suctioning positions 52 and 53 through the openings 54c and 54d. As illustrated, a front cover 55 is removably fitted on the near side of the transport region B (Y-axis negative direction). Accordingly, an area near the center of the transport region B is covered with a cover portion including the roof 54 and the front cover 55.

According to the transport unit 50 structured as above, upper sides of the sample rack L and the sample container T on the transport region B are left unexposed except the areas of the openings 54a and 54b. This structure prevents foreign matters from entering the sample container T in the transport region B from an upper direction, and also prevents the operator from contacting the sample rack L and the sample container T. The transport unit 50 structured as described above can avoid any contact possibly made by the operator with the sample rack L and the sample container T near the center of the transport region B (area covered with the roof 54 and the front cover 55). Thus, the operator can be prevented from contacting the sample rack L and the sample container T.

The pre-read position illustrated in FIG. 4 is included in the area covered with the roof 54 and the front cover 55. Therefore, when the sample rack L is positioned at the pre-read position, the sample rack L is entirely covered by the roof 54 and the front cover 55. The transport suspending position illustrated in FIG. 4 is also included in the area covered with the roof 54 and the front cover 55. In the case where, for example, the left end of the sample rack L sticks out of the front cover 55 when the sample of the sample rack L is suctioned, the sample rack L can be positioned at the transport suspending position under the roof 54 and the front cover 55 in response to occurrence of the first suspension event described later. This further ensures the avoidance of any contact made by the operator with the sample rack L and the sample container T during the suspension of measuring operation.

FIG. 7 is a diagram illustrating a circuit configuration of the measurement device 2.

The measurement device 2 includes a controller 200, a barcode reader 51, a dispensing unit stepping motor unit 211, a dispensing unit rotary encoder unit 212, a motor drive circuit 213, a rack transverse feed mechanism stepping motor unit 221, a rack transverse feed mechanism rotary encoder unit 222, a motor drive circuit 223, an air cylinder B34, a temperature detector 231, a reagent residual quantity detector 232, a liquid quantity detector 233, a cuvette storage quantity detector 234, a rack detector 235, a sensor unit 236, and a measurement unit drive unit 237.

The controller 200 includes a CPU 201, a ROM 202, a RAM 203, a hard disc 204, a communication interface 205, and an I/O interface 206.

The CPU 201 runs a computer program stored in the ROM 202 and a computer program loaded in the RAM 203. The RAM 203 is used to read computer programs recorded in the ROM 202 and the hard disc 204. The RAM 203 is also used as a working region of the CPU 201 when these computer programs are run. The hard disc 204 stores therein various computer programs to be run by the CPU 201, for example, an operating system and an application program, and data used to run these computer programs. Through the communication interface 205, data can be transmitted and received to and from the information processing device 3.

The CPU 201 is connected via the I/O interface 206 to the barcode reader 51, dispensing unit rotary encoder unit 212, motor drive circuit 213, rack transverse feed mechanism rotary encoder unit 222, motor drive circuit 223, air cylinder B34, temperature detector 231, reagent residual quantity detector 232, liquid quantity detector 233, cuvette storage quantity detector 234, rack detector 235, sensor unit 236, and measurement unit drive unit 237.

The dispensing unit stepping motor unit 211 includes stepping motors 211a and 211b which independently rotate the support member 21a of the sample dispensing unit 21 and the support member 22a of the sample dispensing unit 22. The dispensing unit rotary encoder unit 212 includes rotary encoders 212a and 212b provided for the stepping motors 211a and 211b of the sample dispensing units 21 and 22. The motor drive circuit 213 is controlled by the CPU 201 to drive the stepping motors 211a and 211b included in the dispensing unit stepping motor unit 211.

The rack transverse feed mechanism stepping motor unit 221 includes the stepping motors B43 of the two rack transverse feed mechanisms B2. The rack transverse feed mechanism rotary encoder unit 222 includes the rotary encoders B44 of the two rack transverse feed mechanisms B2. The motor drive circuit 223 is controlled by the CPU 201 to independently drive the two stepping motors B43 included in the rack transverse feed mechanism stepping motor unit 221.

The rotary encoders constituting the dispensing unit rotary encoder unit 212 and the rack transverse feed mechanism rotary encoder unit 222 are incremental encoders. The rotary encoder is configured to output a pulse signal depending on a rotational displacement of the stepping motor. The rotational speed of the stepping motor can be detected by counting the number of pulses outputted from the rotary encoder.

The temperature detector 231 is provided with a temperature sensor to detect a temperature of the warming table 16. The reagent residual quantity detector 232 is provided with a liquid surface detecting sensor to detect respective residual quantities of the reagents in the reagent containers disposed on the reagent table 11, 12. The liquid quantity detector 233 is equipped with a plurality of liquid surface detecting sensors to detect a residual quantity of the washing solution tank containing the washing solution used to wash the sample dispensing units 21 and 22 and the reagent dispensing units 23 to 25, and a waste liquid quantity of the waste washing solution tank containing the wasted solution. The cuvette storage quantity detector 234 is equipped with a cuvette storage sensor to detect a residual storage quantity of the cuvettes housed in the cuvette supply unit 33. The rack detector 235 includes sensors A2, B51 to B55 and C2 provided in the transport unit 50. The sensor unit 236 includes a photosensor which detects that the main body cover 29 is open. To carry out dispensing operations by the sample dispensing units 21 and 22 and the reagent dispensing units 23 to 25, the measurement unit drive unit 237 includes a pneumatic source for supplying pressure to these dispensing units, and a driver for driving the tables (reagent tables 11 and 12, cuvette table 15, and warming table 16).

Figure 8:
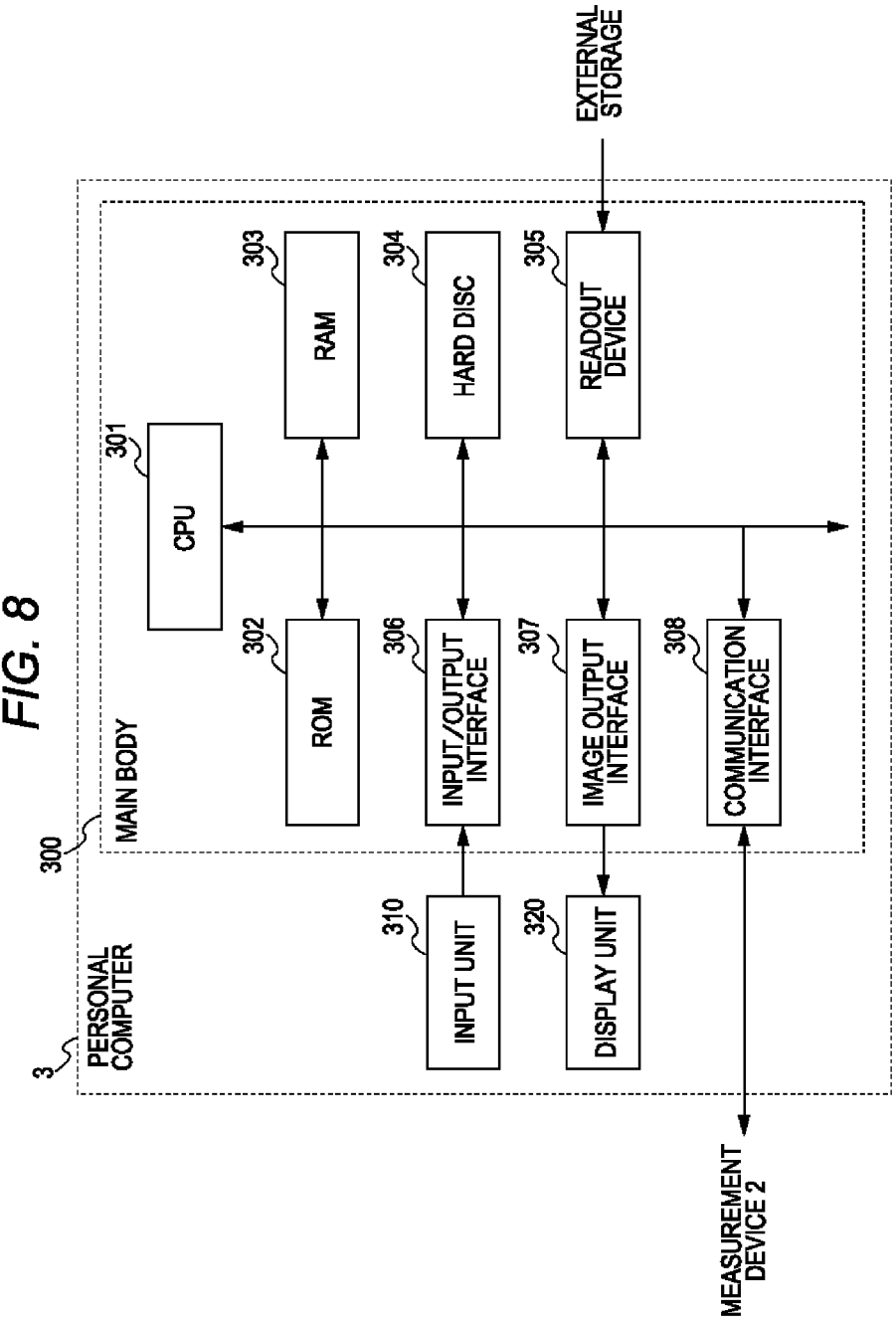
FIG. 8 is a diagram illustrating a circuit configuration of an information processing device according to the embodiment.

FIG. 8 is a diagram illustrating a circuit configuration of the information processing device 3.

The information processing device 3 includes a personal computer and also includes a main body 300, an input unit 310, and a display unit 320. The main body 300 includes a CPU 301, a ROM 302, a RAM 303, a hard disc 304, a readout device 305, an input/output interface 306, an image output interface 307, and a communication interface 308.

The CPU 301 runs a computer program stored in the ROM 302 and a computer program loaded in the RAM 303. The RAM 303 is used to read computer programs recorded in the ROM 302 and the hard disc 304. The RAM 303 is also used as a working region of the CPU 301 when these computer programs are run.

The hard disc 304 stores therein various computer programs to be run by the CPU 301, for example, an operating system and an application program, and data used to run these computer programs. Specifically, in the hard disc 304, there are installed a display program for receiving a reagent condition in the measurement device 2 to, for example, display a message notifying the reagent residual quantity on the display unit 309, and operation programs for replacing the reagent or operating the measurement device 2 in accordance with additional operation commands.

The readout device 305 includes, for example, a CD drive or a DVD drive. The readout device 305 can read computer programs and data recorded on a recording medium. The input unit 310 including a mouse and a keyboard is connected to the input/output interface 306. The operator inputs data to the information processing device 3 by using the input unit 310. The image output interface 307 is connected to the display unit 320 including, for example, a display screen to output a video signal suitable for image data to the display unit 320. The display unit 320 displays an image based on the inputted video signal. Through the communication interface 308, data can be transmitted and received to and from the measurement device 2.

Figure 9:
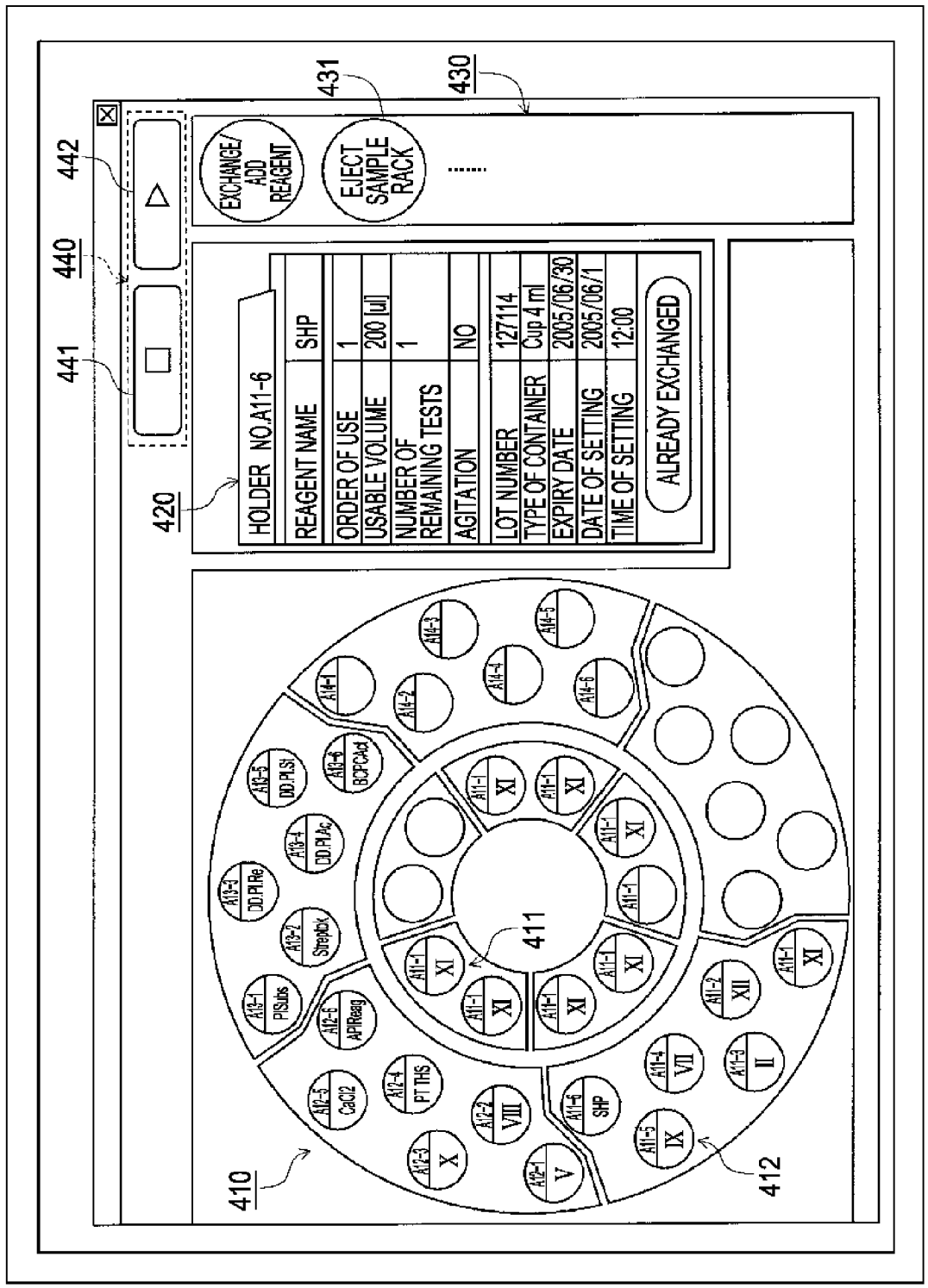
FIG. 9 is a diagram illustrating an example of a reagent information screen displayed on a display unit of the information processing device according to the embodiment.

FIG. 9 is a diagram illustrating an example of a reagent information screen displayed on the display unit 320 of the information processing device 3. The reagent information screen includes a location display region 410, a detailed information display region 420, an operation command display region 430, and an operation decision display region 440.

The location display region 410 displays the positions of the container racks 13 and 14 on the reagent tables 11 and 12, and a condition of the reagent containers housed in these container racks.

When a reagent mark 411 or 412 in the location display region 410 is selected, detailed information on contents of the reagent container retained at the position of the selected mark is displayed in the detailed information display region 420.

The operation command display region 430 has a plurality of different command buttons including a sample rack ejection button 431. When the operator presses any of the buttons, an operation corresponding to the pressed button is carried out.

The measurement command display region 440 has a measurement suspending button 441 and a measurement start button 442. When the operator presses the measurement suspending button 441, a measurement suspension processing is carried out. When the operator presses the measurement start button 442 during the suspension of the measurement, a measurement restart processing is carried out. The measurement start button 442 is displayed in active state as far as the measurement can restart. When the measurement start button 442 is pressed whenever the measurement restart is infeasible, a message is displayed on the screen so that the operator is notified of the failure to restart the measurement.

Next, the processing operation of the sample processing apparatus is described. The following processing operation, which is controlled by the information processing device 3, is carried out through data communicated between the measurement device 2 and the information processing device 3.

Figure 10:
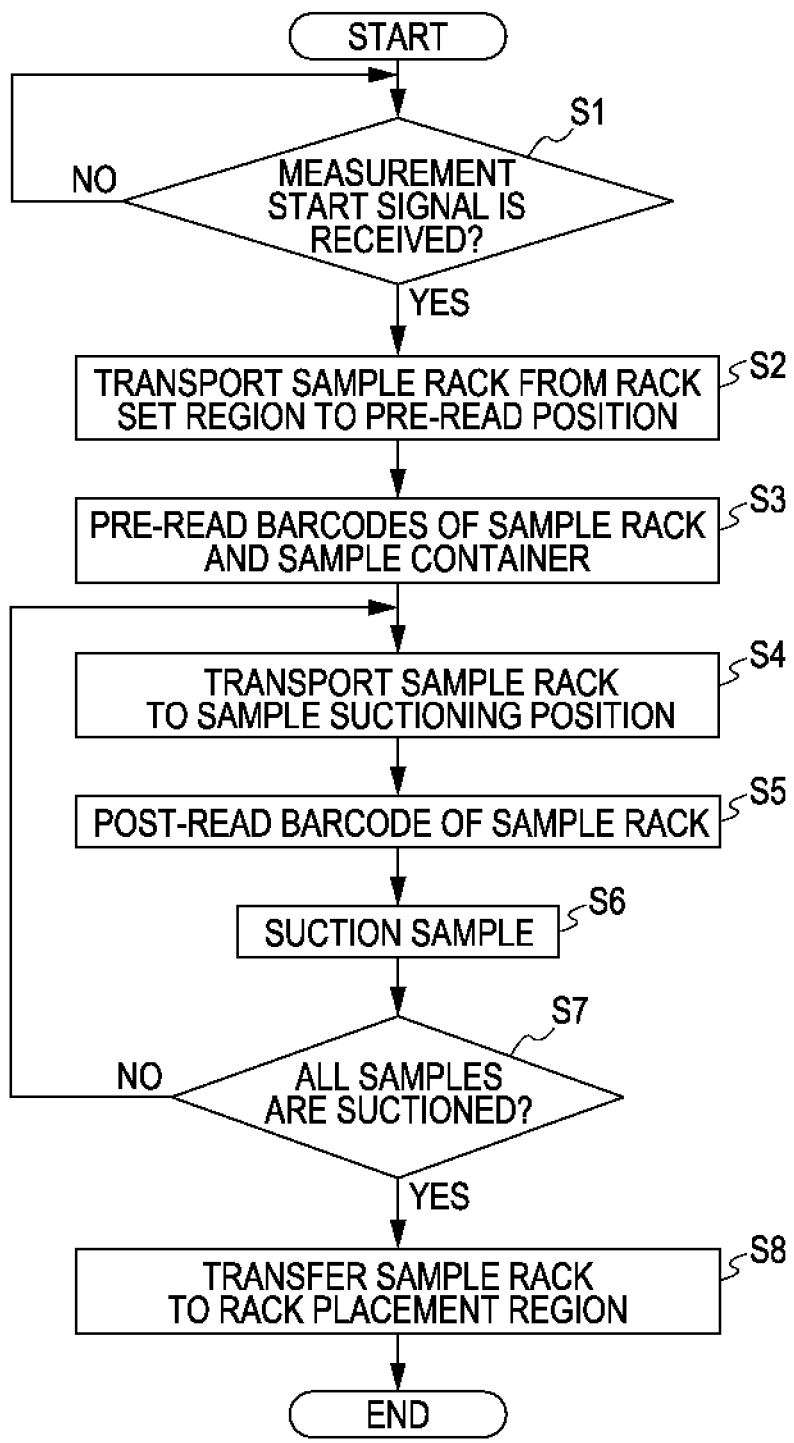
FIG. 10 is a flowchart illustrating a sample suctioning processing according to the embodiment.

FIG. 10 is a flowchart illustrating steps of a sample suctioning processing according to the present embodiment. In the processing flow described below, the transport position of the sample rack L is known from the output of the rack transverse feed mechanism rotary encoder unit 222 and the output of the rack detector 235.

In the present embodiment, when the operator inputs a measurement start command via the information processing device 3, the measurement device 2 starts its measuring operation. When the CPU 201 of the measurement device 2 receives a measurement start signal from the information processing device 3 (S1: YES), the CPU 201 transports the sample rack L from the rack set region A to the pre-read position (S2). At the pre-read position, the barcode reader 51 performs the pre-read of the barcode label BL2 of the sample rack L and the barcode label BL1 of the sample container T held in the sample rack L (S3).

The sample rack L, for which the barcode pre-read at the pre-read position is completed, is transported to the sample suctioning position 52 or 53 (S4). When the sample container T is positioned at the sample suctioning position 52 or 53, the barcode reader 51 performs the post-read of the barcode label BL1 affixed to the sample container T (S5). The sample of the barcode-read sample container T is suctioned by the sample dispensing unit 21 or 22 at the sample suctioning position 52 or 53 (S6).

After the samples in all of the sample containers T held in the sample rack L are suctioned (S7: YES), the sample rack L is transported to the rack placement region C (S8), and the sample suctioning processing for the sample rack L ends. Unless the samples in all of the sample containers T held in the sample rack L are suctioned (S7: NO), steps S4 to S6 are repeatedly carried out until the samples in all of the sample containers T held in the sample rack L are suctioned.

In the case where there is a subsequent sample rack L that follows the sample rack L currently positioned at the sample suctioning position 52 or 53, the processing steps in S2 and after S2 start for the subsequent sample rack L. In this case, the barcode reader 51 is moved in the X-axis positive and negative directions to post-read the preceding sample rack L with a higher priority but pre-read the subsequent sample rack L as well.

Figure 11A:
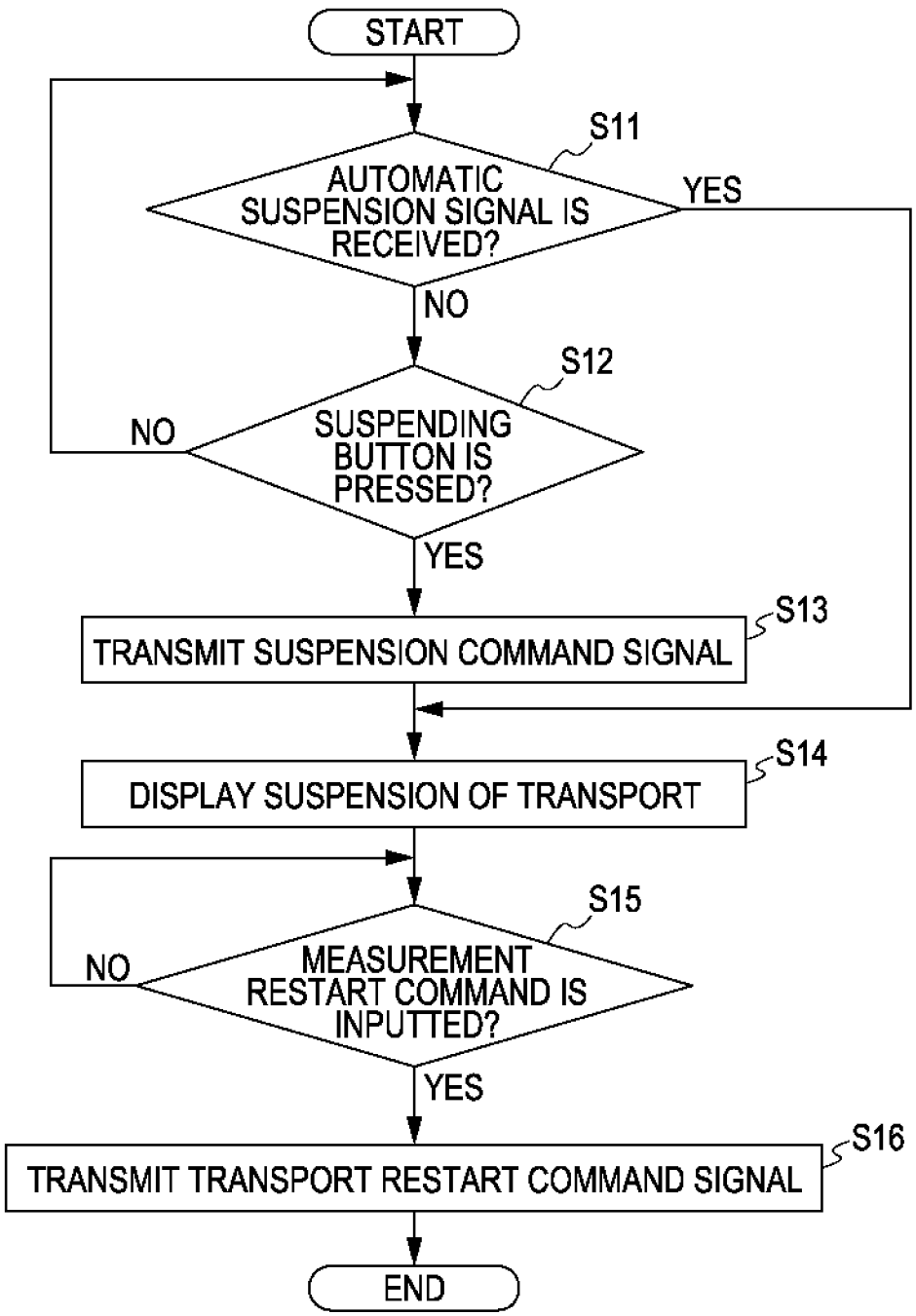
FIGS. 11A and 11B are flowcharts illustrating a suspension and restart processing according to the embodiment.
Figure 11B:
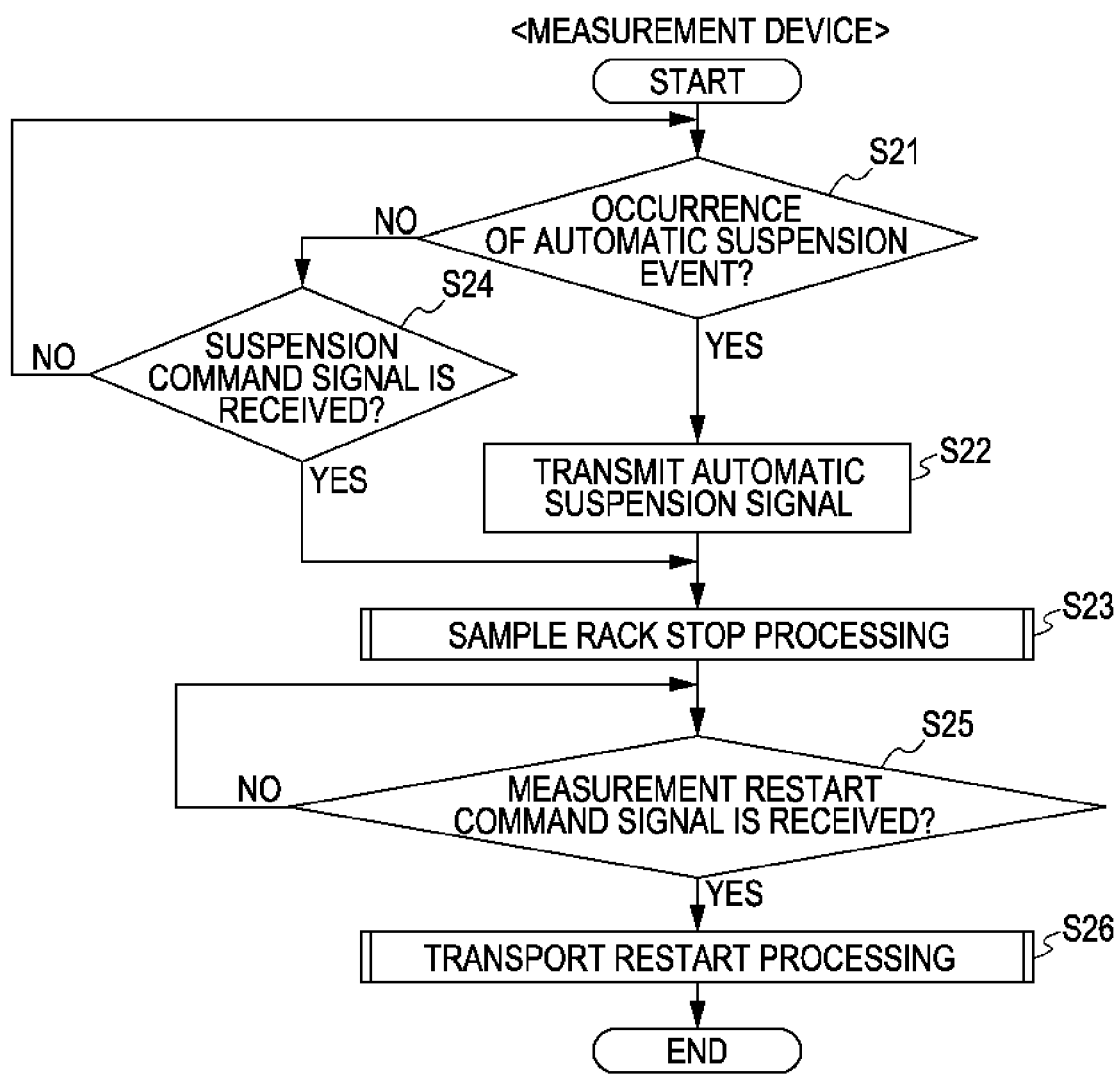

FIGS. 11A and 11B are flowcharts illustrating processing steps of a transport suspension and restart processing carried out by the measurement device 2 and the information processing device 3.

In the present embodiment, when the operator presses the measurement suspending button 441 illustrated in FIG. 9 to transmit the suspension command signal from the information processing device 3 to the measurement device 2, the transport operation of the sample rack is suspended. Having detected the occurrence of a predetermined transport automatic suspension event, more specifically, cuvette shortage detected by the cuvette storage quantity detector 234, filled-up waste solution tank detected by the liquid quantity detector 233, washing solution shortage detected by the liquid quantity detector 233, reagent shortage detected by the reagent residual quantity detector 232, or rack placement region C filled with sample racks L detected by the sensor C2 of the rack detector 235, the transport operation of the sample rack is suspended.

Referring to FIG. 11A, when the CPU 301 of the information processing device 3 receives a signal indicating the detection of any of the transport automatic suspension events (automatic suspension signal) from the measurement device 2 (S11: YES), the CPU 301 makes the display unit 320 of the information processing device 3 display thereon that the measuring operation was suspended (S14). When the operator presses the measurement suspending button 441 (S12: YES), the CPU 301 of the information processing device 3 transmits a suspension command signal to the measurement device 2 (S13). Then, the CPU 301 makes the display unit 320 of the information processing device 3 display thereon that the measurement was suspended (S14).

Figure 12:
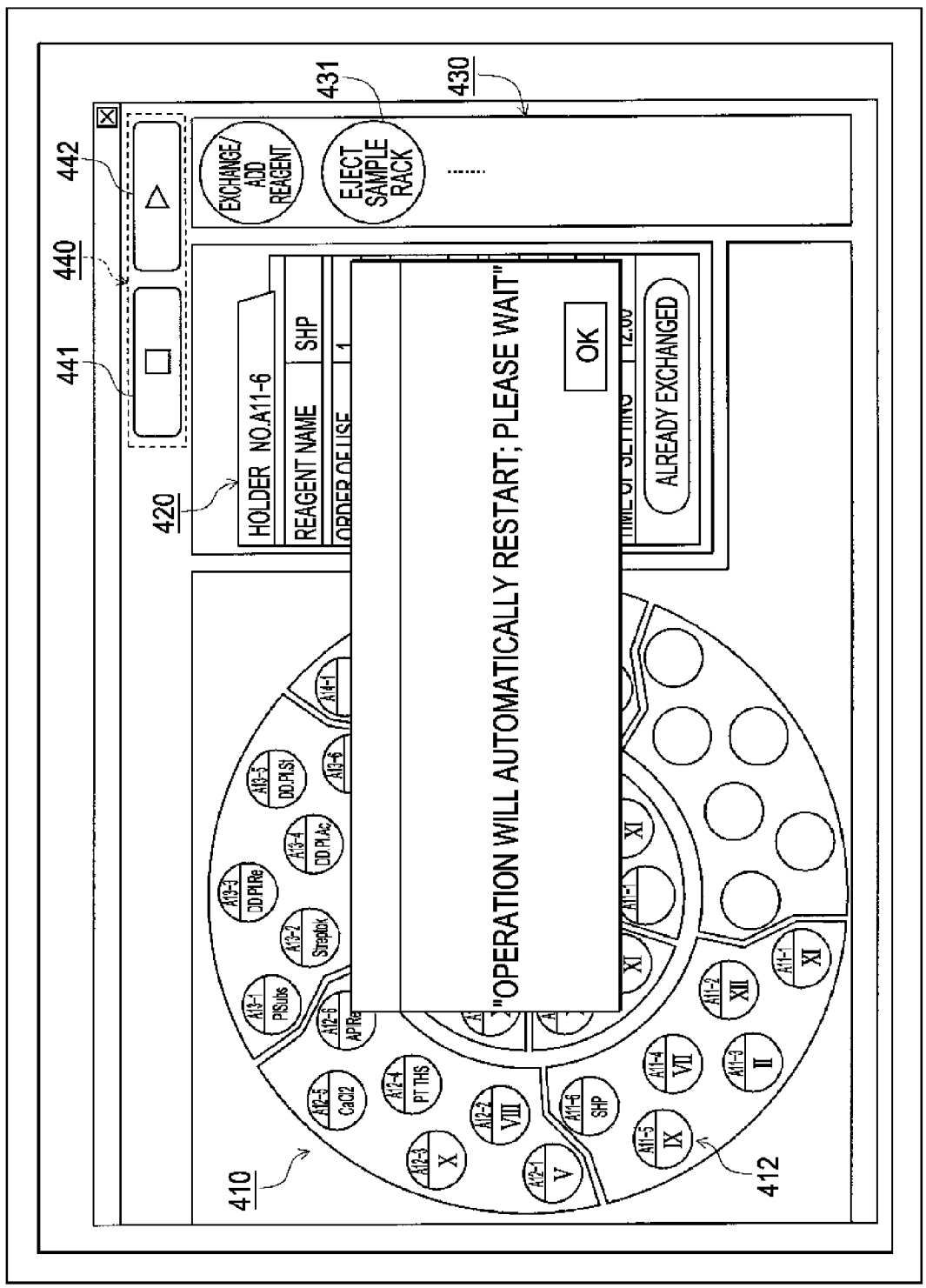
FIG. 12 is a diagram illustrating an example of a measurement suspension message displayed on the display unit of the information processing device according to the embodiment.

FIG. 12 is a diagram illustrating an example of the measurement suspension message displayed on the display unit 320 of the information processing device 3; wherein "the operation will automatically restart; please wait" is displayed. The message to be displayed may be "it is unnecessary to transport the sample rack; the transport of the sample rack will automatically start again when the measurement restarts". The operator can accordingly know it is unnecessary to reset the sample rack L in the rack set region A.

Referring to FIG. 11B, when the CPU 201 of the measurement device 2 detects any of the transport automatic suspension events (S21: YES), the CPU 201 transmits the automatic suspension signal to the information processing device 3 (S22), and stops the sample rack L by executing a "sample rack stop processing" (S23). When the CPU 201 of the measurement device 2 receives the suspension command signal from the information processing device 3 (S24: YES), the CPU 201 stops the sample rack L by executing a "sample rack stop processing" (S23). The "sample rack stop processing" will be described later with reference to FIG. 16.

Referring to FIG. 11A, when the operator commands to restart the measuring operation by the measurement device 2 via the information processing device 3 (S15: YES), the CPU 301 of the information processing device 3 transmits a measurement restart command signal to the measurement device 2 (S16), and ends the processing.

Referring to FIG. 11B, when the CPU 201 of the measurement device 2 receives the measurement restart command signal from the information processing device 3 (S25: YES), the CPU 201 restarts the transport operation of the sample rack L by executing a "transport restart processing" (S26), and then ends the processing steps. The "transport restart processing" will be described later with reference to FIG. 17.

In the case where the sample rack L is possibly positionally shifted during the time when the transport operation of the sample rack L temporarily stops and then restarts, it may be determined during this period of time whether or not the sample rack L is positionally shifted.

Figure 13:
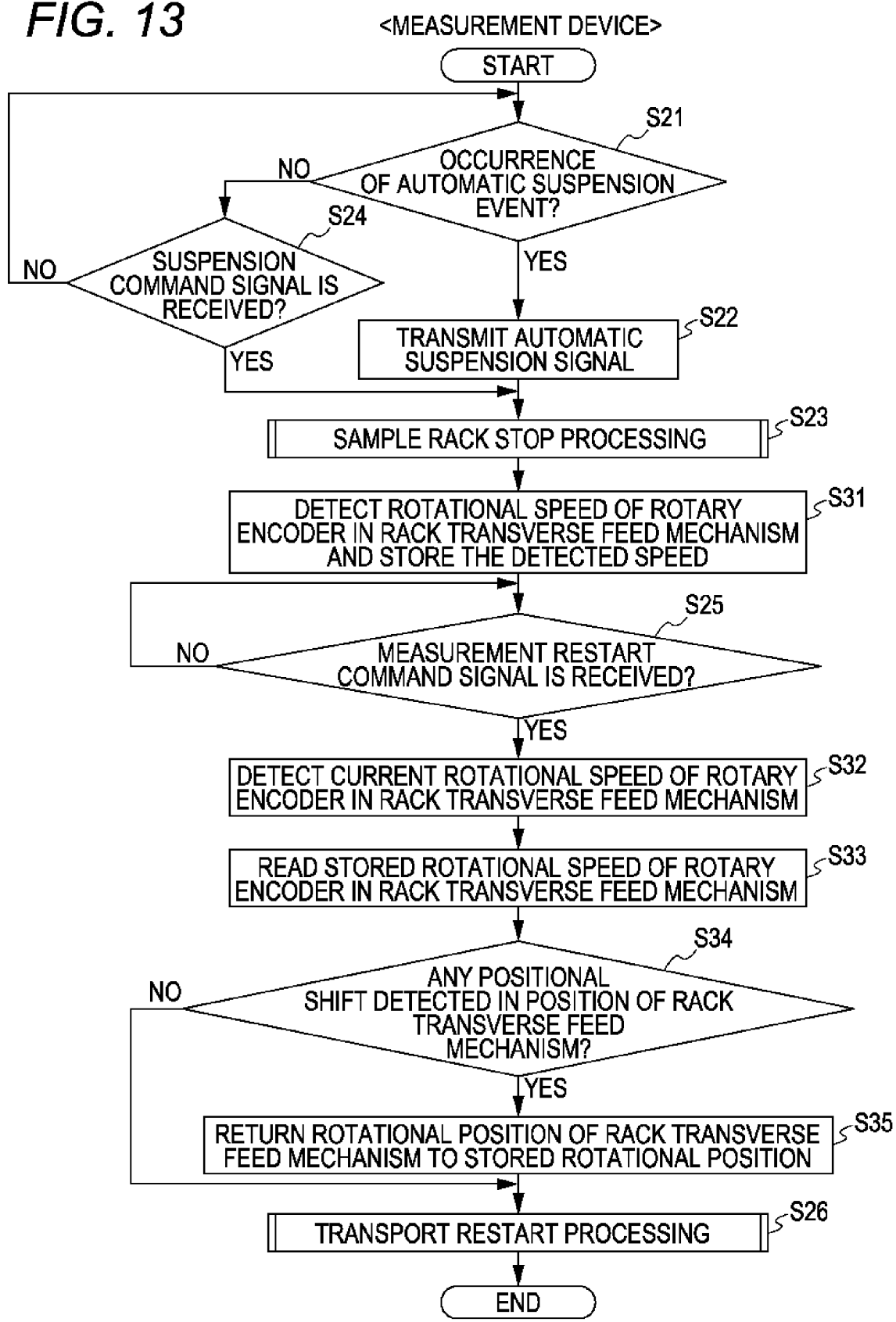
FIG. 13 is a modified example of a flowchart illustrating the suspension and restart processing according to the embodiment.

FIG. 13 is a modified flowchart illustrating processing steps of suspending and restarting the transport of the sample rack L by the CPU 201 of the measurement device 2. Only the processing steps which are different to the flow of the processing steps illustrated in FIG. 11A are described below.

In S31, the position of the sample rack L on the transport region B stopped by the "sample rack stop processing" is stored. More specifically, the rotational speed detected from the rotary encoder B44 of the rack transverse feed mechanism B2 which transports the sample rack L is stored in the RAM 303 or the hard disc 304 of the information processing device 3.

When the measurement restart is commanded (S25: YES), the current rotational speed of the rotary encoder B44 of the rack transverse feed mechanism B2 is detected (S32), and the rotational speed stored in S31 is read out (S33). When these two rotational speeds are compared to each other and determined that the rack transverse feed mechanism B2 is positionally shifted (S34: YES), the rack transverse feed mechanism B2 is returned to its position based on the rotational speed stored in S31 (S35).

Accordingly, in the case where the rack transverse feed mechanism B2 is positionally shifted immediately after the sample rack L was stopped, the rack transverse feed mechanism B2 can be returned to its proper position before the "transport restart processing" restarts the transport operation of the sample rack L. As a result, the transport operation of the sample rack L can smoothly restart.

FIG. 14A and FIG. 14B respectively illustrate a transport operation control list of a preceding rack and a transport operation control list of a subsequent rack. Of the two sample racks L currently transported in the transport region B, the sample rack L disposed downstream (X-axis positive direction) is the preceding rack, and the sample rack L disposed upstream (X-axis negative direction) is the subsequent rack.

The transport operation control list includes items of, for example, rack position, holding position, sample barcode read state, measurement mode, and suctioning state as illustrated in FIGS. 14A and 14B. The transport operation control list is stored in the RAM 203 or hard disc 204 of the measurement device 2. According to the transport operation control list, the transport operation of the pre-read sample rack L is controlled.

The item of "measurement mode" in the transport operation control list is obtained from a job list described later based on information of the barcode label BL2 of the sample rack L pre-read at the pre-read position. The job list retains therein measurement order information including respective sample measurement modes, measurement state information, and measurement results. The job list is updated when the sample container T newly measured is registered in the job list (hereinafter, referred to as "order-register"), when the measurement starts, and when the measurement result is obtained. As illustrated in FIG. 15, the measurement mode stored in the job list is linked to the rack number and the holding position of the sample container T (rack number-position). When the barcode label BL2 of the sample rack L is read at the pre-read position, the measurement mode linked to the holding position relevant to the rack number corresponding to the read barcode label BL2 is transcribed from the job list in the item of "measurement mode" of the subsequent rack. The item of "suctioning state" in the transport operation control list is updated from "unfinished" to "finished" when the sample is suctioned in S6 of FIG. 10.

Referring to FIG. 14A, it is known from the item of "rack position" that the preceding rack is at the sample suctioning position 52. It is known from the item of "sample barcode read state" that the pre-read by the barcode reader 51 has already been done for all of the holding positions. It is known from the item of "measurement mode" that standard measurement is performed for the sample containers T at the holding positions 1 to 4 and 7 to 10, and trace-level measurement is performed for the sample containers T at the holding positions 5 and 6. It is known from the item of "suctioning state" that the sample suctioning is already finished for the sample containers T at the holding positions 1 to 5, but the sample suctioning is still unfinished for the sample containers T at the holding positions 6 to 10.

Referring to FIG. 14B, it is known from the item of "rack position" that the subsequent rack is positioned at the pre-read position. It is known from the item of "sample barcode read state" that the pre-read by the barcode reader 51 has already been finished for the holding positions 1 to 5, but the pre-read by the barcode reader 51 is still unfinished for the holding positions 6 to 10. It is known from the item of "measurement mode" that standard measurement is performed for the sample containers T at the holding positions 1 to 3, 6 and 9 in the subsequent rack, and trace-level measurement is performed for the sample containers T at the retaining positions 4, 5, 7, 8 and 10 in the subsequent rack. It is known from the item of "suctioning state" that the sample suctioning is finished for none of the retaining positions.

When the preceding rack is transported to the rack placement region C and the subsequent rack at the pre-read position is positioned at the sample suctioning position 52 or 53, the transport operation control list of the preceding rack is overwritten with the transport operation control list of the subsequent rack, and the transport operation control list of the subsequent rack is initialized. When the next sample rack L is positioned at the pre-read position, the transport operation control list for the sample rack L subsequent thereto is created.

FIG. 15 is a diagram illustrating the job list.

As illustrated in the figure, the job list retains therein information such as measurement state, measurement order information, and measurement result of the sample container T which was order-registered. The job list is stored in the hard disc 304 of the information processing apparatus 3.

The job list includes items of, for example, state, rack number-position, sample number, measurement mode, date, time, and PT % (measurement result). The sample measurement state is written in the item of "state". For the sample just order-registered but not yet measured, the item of "state" shows "pending". When the sample rack L is ejected as described later, the item shows "error". When the sample measurement is terminated, the item of "state" becomes blank. The item of "rack number-position" shows a number affixed to the sample rack L for discrimination and a holding position of the sample container T. Each of the rack numbers is linked to information of the barcode label BL2 of the sample rack L. The item of "sample number" shows a number affixed to the sample container T for discrimination. Each of the "sample numbers" is linked to information of the barcode label BL1 of the sample container T. The items of "date" and "time" show a date and a time point when the sample is fetched into the measurement device 2. When the measuring operation is normally terminated, its measurement result is written in the item of "PT %". In the case where the measuring operation is not normally terminated, "***.*" (mask) is written in the item of "PT %". "PT %" is an example of possible measurement items, and the job list includes other measurement items.

Figure 16:
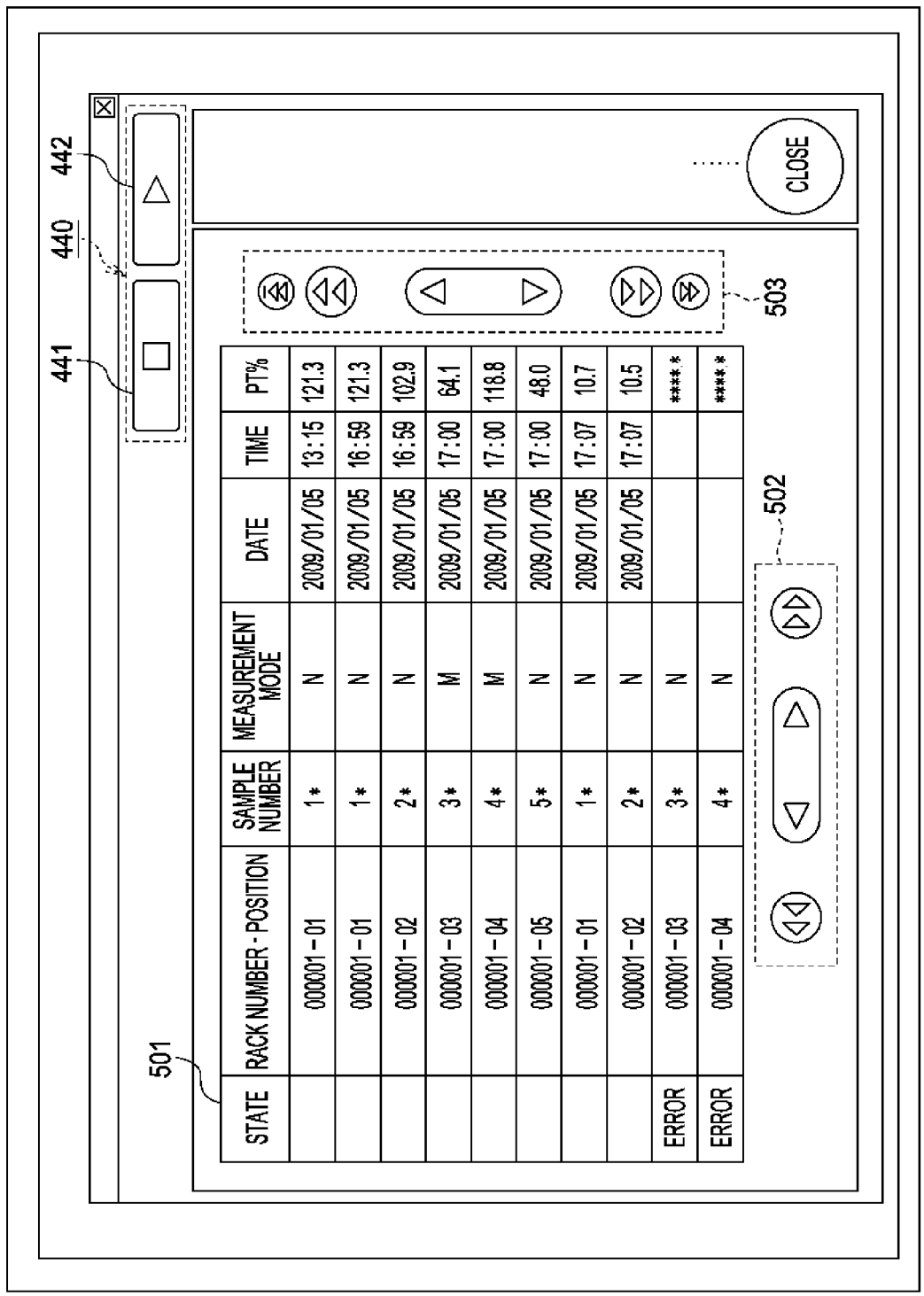
FIG. 16 a diagram illustrating an example of a screen based on the job list displayed on the display unit of the information processing device according to the embodiment.

FIG. 16 illustrates an example of the job list display screen displayed on the display unit 320 of the information processing device 3 based on the job list. The job list screen includes, in addition to the measurement command display region 440 illustrated in FIG. 9, a job list display unit 501 which displays contents of the job list, a horizontal scroll button unit 502, and a vertical scroll button unit 503.

When a button of the horizontal scroll button unit 502 is pressed, the job list display unit 501 displays other items adjacent on right and left to the item currently displayed. When a button of the vertical scroll button unit 503 is pressed, the job list display unit 501 displays other job contents above and below of the job contents currently displayed.

Figure 17:
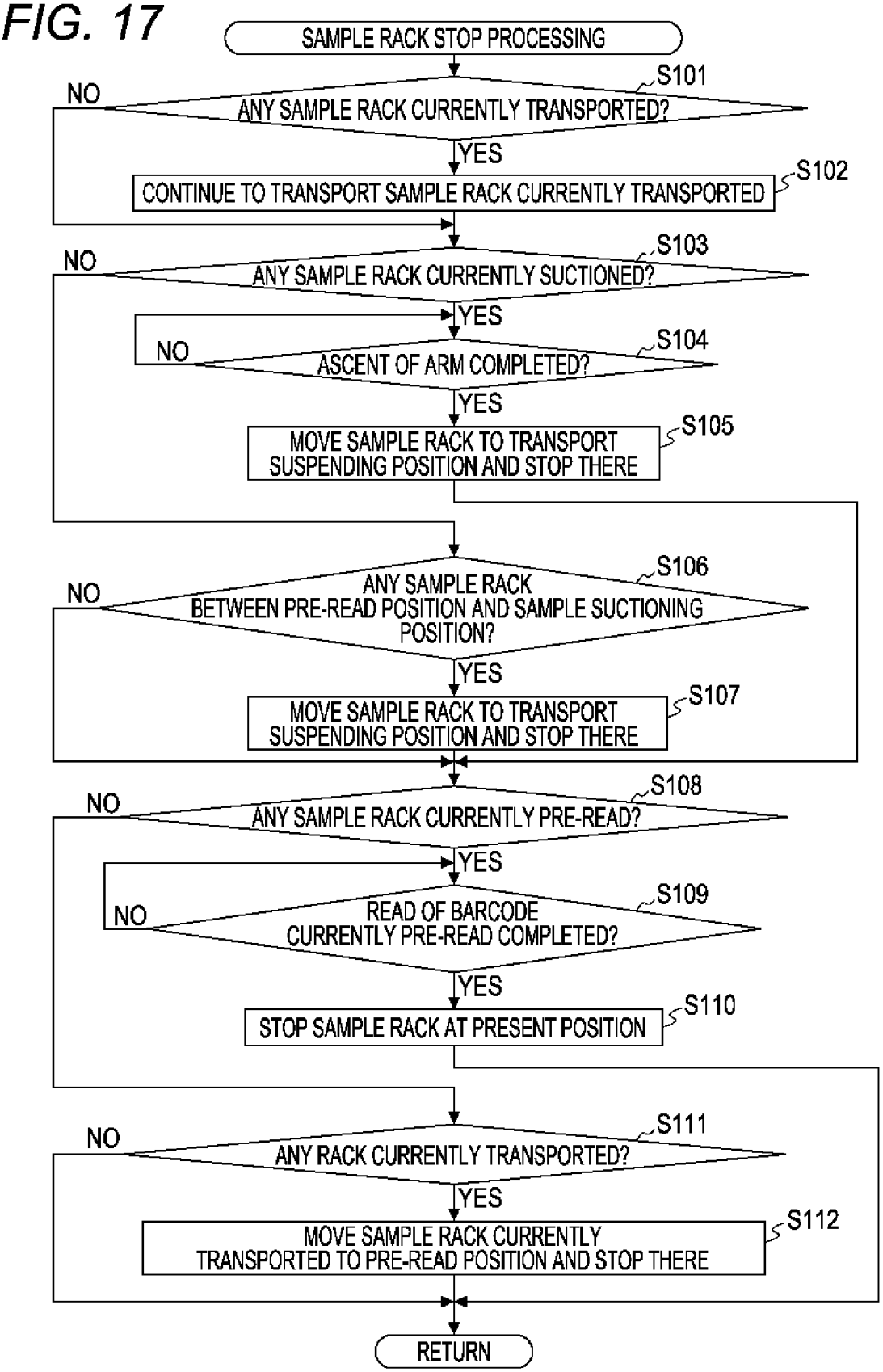
FIG. 17 is a flowchart illustrating a sample rack stop processing according to the embodiment.

FIG. 17 is a flowchart illustrating processing steps of the "sample rack stop processing" in the suspension and restart processing illustrated in FIG. 11B.

At the time of occurrence of a transport suspension event, when the samples in all of the sample containers T in one sample rack L have been suctioned and there is another sample rack L currently transported to the rack placement region C (S101: YES), the sample rack L is transported to the rack placement region C (S102).

When the sample of any sample rack L is currently suctioned at the sample suctioning position 52 or 53 (S103: YES), the arm of the sample dispensing unit 21 or 22 is ascended. When the ascent of the arm of the sample dispensing unit 21 or 22 is completed (S104: YES), the sample rack L is transported to the transport suspending position illustrated in FIG. 4 to stop there (S105). The sensor B55 detects that the sample rack L was transported to the transport suspending position.

In the presence of any sample rack L between the pre-read position and the sample suctioning position 52 or 53 (S106: YES) while there is no sample rack L currently subject to the sample suctioning at the sample suctioning position 52 or 53, (S103: NO), the sample rack L is transported to the transport suspending position to stop there (S107). Thus, the sample rack L already pre-read and currently transported to the sample suctioning position 52 or 53 is positioned at the transport suspending position.

In the presence of the sample rack L currently pre-read at the pre-read position (S108: YES), the sample rack L stays at the pre-read position until the currently ongoing pre-read of the barcode of the sample container T or sample rack L is finished. After the read of the barcode of the sample container T or the sample rack L currently pre-read is finished (S109: YES), the sample rack L stops at the position (S110).

In presence of the sample rack L currently transported by the rack feed mechanism A1 in the rack set region A or the sample rack L currently transported to the pre-read position in the transport region B (S111: YES) while there is no sample rack L currently pre-read at the pre-read position (S108: NO), the sample rack L is transported to the pre-read position to stop there (S112). The sensor B52 detects that the sample rack L has been transported to the pre-read position. Then, the "sample rack stop processing" ends.

By the time when the transport operation restarts after the sample rack L is stopped in S105, S107, S110, and S112, the engagement claws B32a of the rack transverse feed mechanisms B2 illustrated in FIG. 5 remain engaged with the sample rack L. During such stoppage period, the stepping motor B43 is continuously excited so that the sample rack L can be prevented from positionally shifting. Accordingly, the transport operation of the sample rack L can restart without any trouble.

Figure 18:
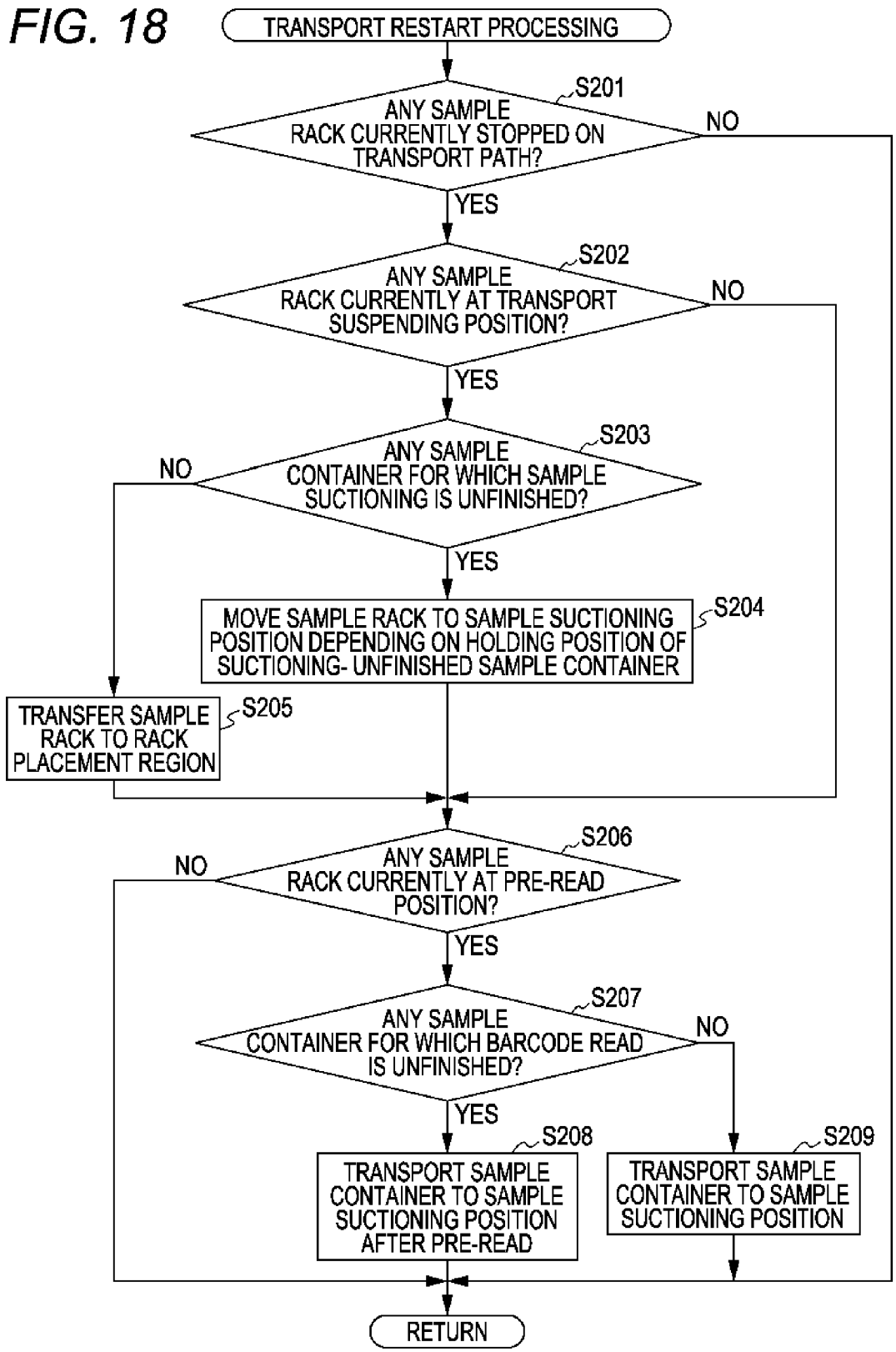
FIG. 18 is a flowchart illustrating a transport restart processing according to the embodiment.

FIG. 18 is a flowchart illustrating processing steps of the "transport restart processing" in the suspension and restart processing illustrated in FIG. 11.

In S201, it is determined whether there is any sample rack L currently stopped on the transport path B1 of the transport region B. In the presence of the sample rack L currently stopped on the transport path B1 (S201: YES), it is determined whether the sample rack L is at the transport suspending position (S202). In the absence of the sample rack L currently stopped on the transport path B1 (S201: NO), the processing steps end.

When determined that the sample rack L is at the transport suspending position (S202: YES), it is then determined whether or not the sample rack L has any sample containers T for which the sample suctioning is unfinished (S203). When determined that the sample rack L is not at the transport suspending position (S202: NO), a processing step of S206 is carried out.

When determined that the sample rack L has the sample container T for which the sample suctioning is unfinished (S203: YES), the transport operation control list is referred, and the sample rack L is transported to the sample suctioning position 52 or 53 depending on whether the sample in the suctioning-unfinished sample container T is subject to standard measurement or trace-level measurement according to the holding position thereof (S204). When there is no sample container T for which the sample suctioning is unfinished in the sample rack L (S203: NO), the sample rack L is transported to the rack placement region C (S205). In this manner, S204 selectively suctions only the sample container T for which the sample suctioning is unfinished, while skipping the sample container T from which the sample has been suctioned.

In the presence of any sample rack L at the pre-read position (S206: YES), it is determined whether there is any sample container T for which the barcode read by the barcode reader 51 is unfinished (S207). When there is no sample rack L at the pre-read position (S206: NO), the processing steps end.

In the presence of the sample container T for which the barcode read by the barcode reader 51 is unfinished (S207: YES), the barcode of the read-unfinished sample container T is read referring to the transport operation control list. In the case where the barcode read for any sample rack L is unfinished, the barcode of the sample rack L is similarly read. After the barcode read is finished, the sample rack L is transported to the sample suctioning position 52 or 53 (S208). When there is no sample container T for which the barcode read by the barcode reader 51 is unfinished (S207: NO), the sample rack L is transported to the sample suctioning position 52 or 53 (S209). In this manner, S208 reads only the read-unfinished barcode label, while skipping the already read barcode label.

Then, the "transport restart processing" ends.

Figure 19A:
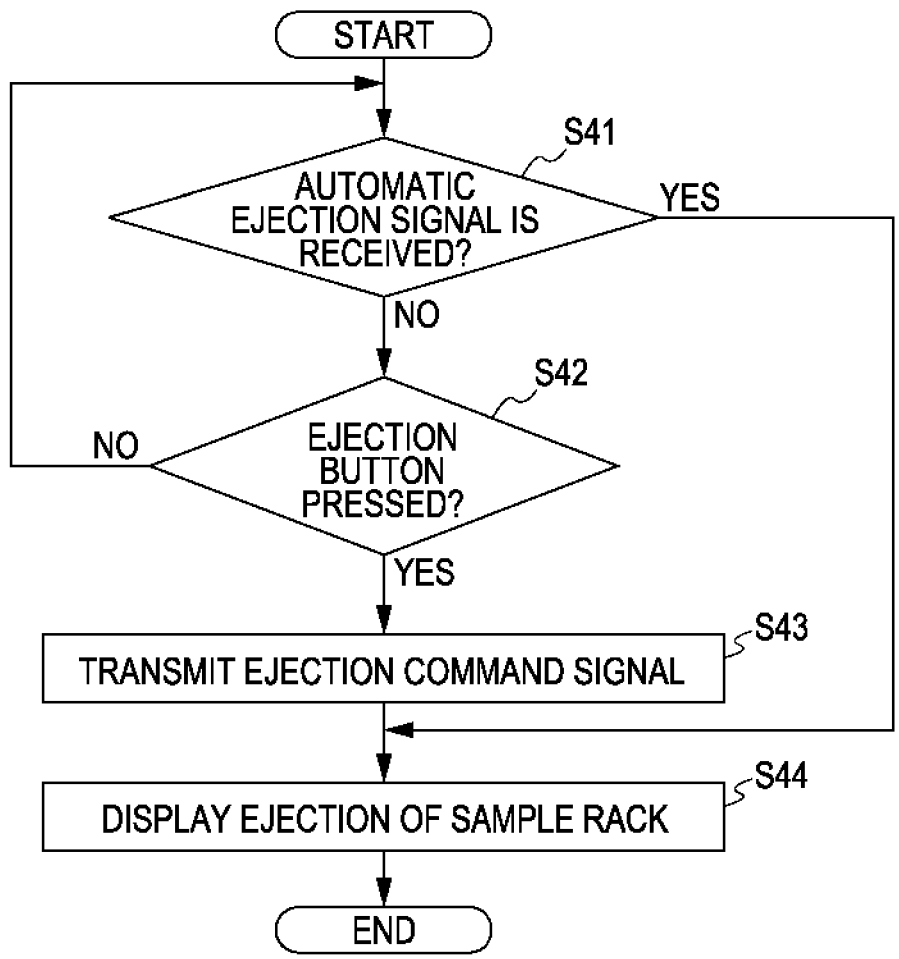
FIGS. 19A to 19C are flowcharts illustrating an ejection processing and a job list display processing according to the embodiment.
Figure 19B:
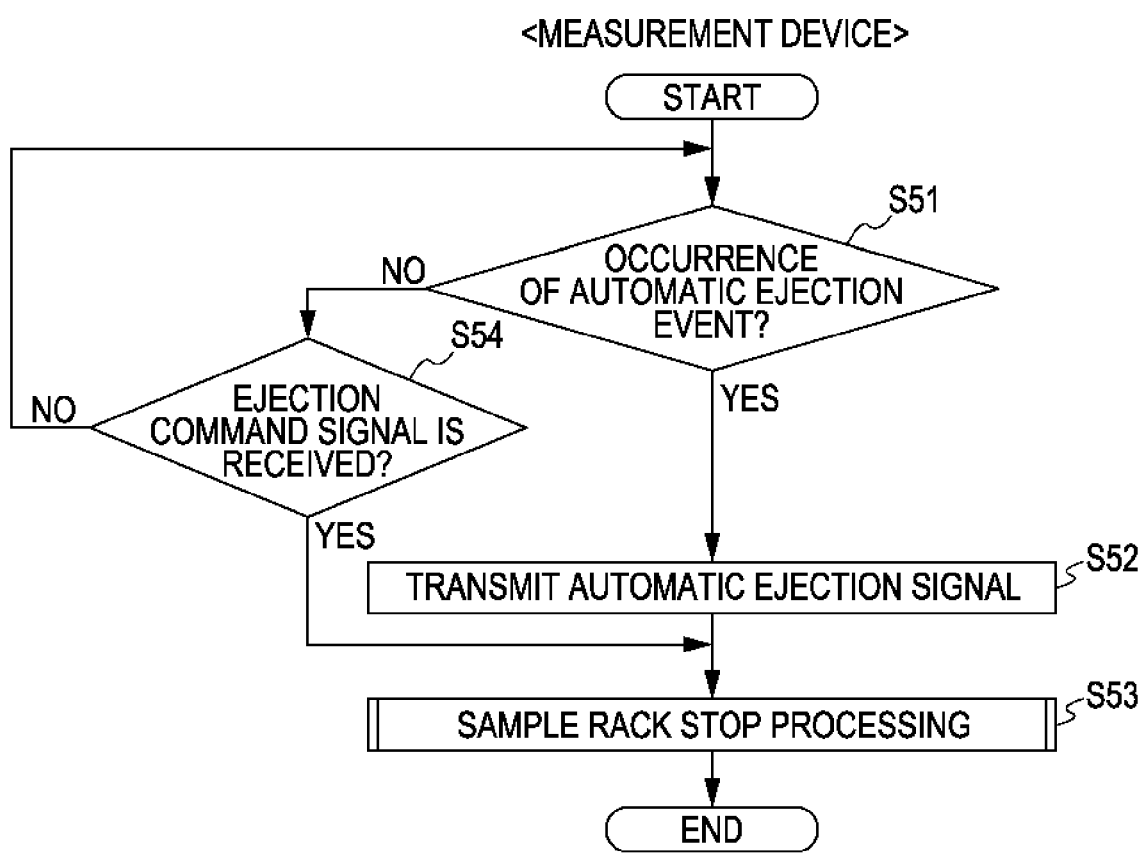

FIGS. 19A and 19B are flowcharts illustrating steps of an ejection processing for ejecting the sample rack L carried out by the measurement device 2 and the information processing device 3.

According to the present embodiment, when the operator presses the sample rack ejection button 431 illustrated in FIG. 9 to transmit the ejection command signal from the information processing device 3 to the measurement device 2, the sample rack L currently transported is ejected into the rack placement region C. The sample rack L currently transported is similarly ejected into the rack placement region C when the state of the measurement device 2 satisfies a predetermined automatic ejection condition, more specifically, when detected by the CPU 201 that operational abnormality of the sample dispensing units 21 and 22 and reagent dispensing units 23 to 25 based on the detection results of the dispensing unit rotary encoder 212, when detected by the CPU 201 that the main body cover 29 is left open based on the detection result of the photosensor in the sensor unit 236, when detected by the CPU 201 that pressure supply abnormality in the pneumatic source of the drive unit 237 of the measurement unit based on the measurement result of the pressure sensor in the sensor unit 236, when detected by the CPU 201 that operational abnormality of the tables (reagent tables 11 and 12, cuvette table 15, and warming table 16) has occurred, and when detected by the CPU 201 that temperature abnormality of the warming table 16 has occurred based on the detection result obtained by the temperature detector 231. Hereinafter, the events that cause the sample rack L to be ejected into the rack placement region C, more specifically; the measurement device 2 receiving the ejection command signal transmitted by the operator via the information processing device 3, and the state of the measurement device 2 satisfying the automatic ejection condition, are collectively called a "second suspension event".

Referring to FIG. 19A, when the CPU 301 of the information processing device 3 receives a signal indicating that the state of the measurement device 2 satisfies the automatic ejection condition (automatic ejection signal) (S41: YES), the CPU 301 makes the display unit 320 of the information processing device 3 display thereon that the sample rack L is ejected (S44). When the sample rack ejection button 431 is pressed by the operator (S42: YES), the CPU 301 of the information processing device 3 transmits the ejection command signal to the measurement device 2 (S43). Then, the CPU 301 makes the display unit 320 of the information processing device 3 display thereon that the sample rack L is ejected (S44), and ends the processing steps.

Figure 20:
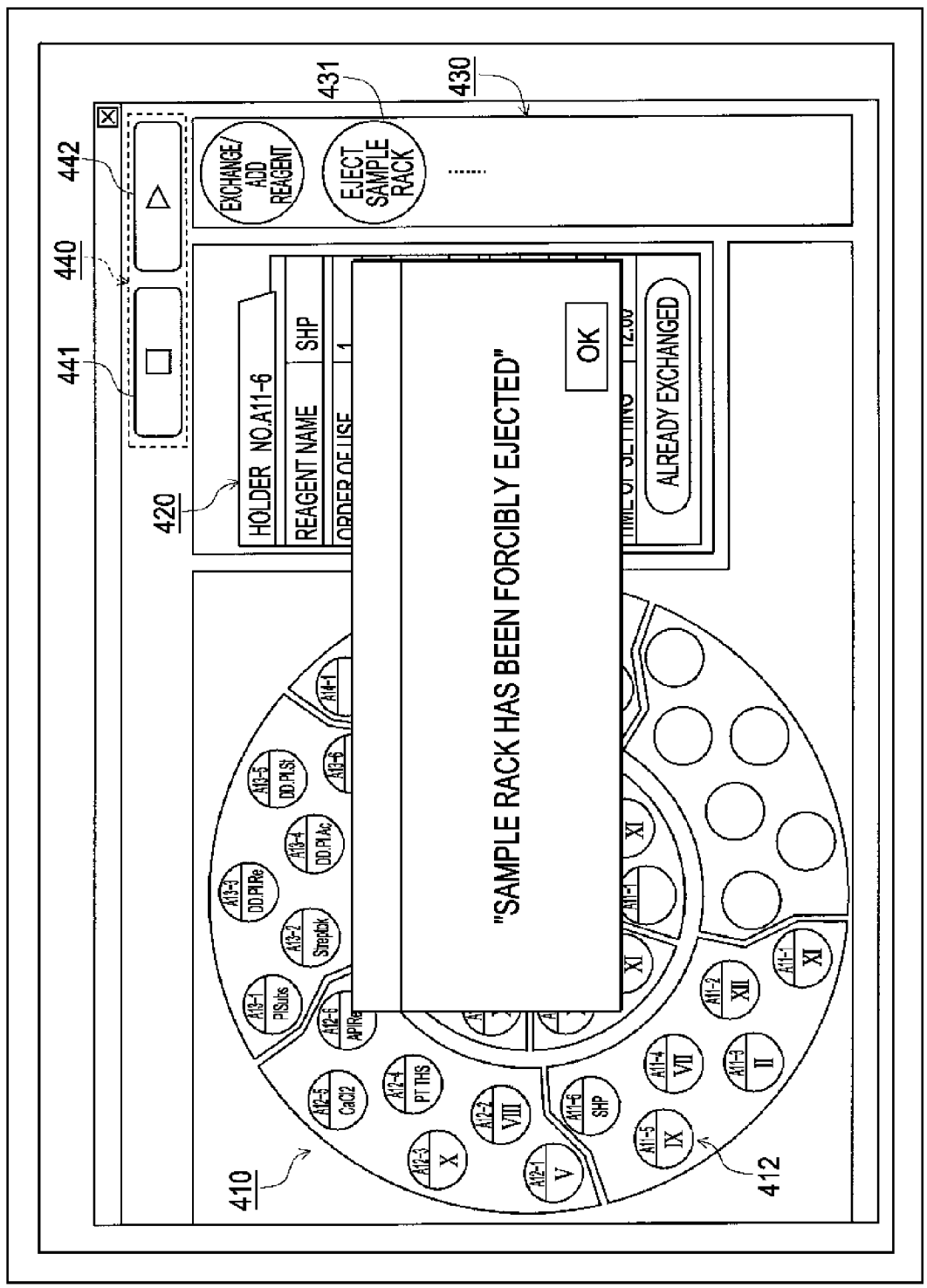
FIG. 20 a diagram illustrating an example of a sample rack ejection message displayed on the display unit of the information processing device according to the embodiment.

FIG. 20 illustrates an example of the message indicating the ejection of the sample rack L displayed on the display unit 320 of the information processing device 3, wherein "sample rack has been forcibly ejected" is displayed. The message to be displayed may be, for example, "the suspension event has occurred, the measuring operation is suspended, and the rack is ejected into the rack placement region". The operator can thereby know that the sample rack L has been ejected into the rack placement region C.

Referring to FIG. 19B, when the CPU 201 of the measurement device 2 detects that the state of the measurement device 2 satisfies the automatic ejection condition (S51: YES), the CPU 201 transmits the automatic ejection signal to the information processing device 3 (S52), and ejects the sample rack L by executing a "sample rack ejection processing" (S53). When the CPU 201 of the measurement device 2 receives the ejection command signal from the information processing device 3 (S54: YES), the CPU 201 ejects the sample rack L by executing the "sample rack ejection processing" (S53). The "sample rack ejection processing" will be described later with reference to FIG. 21.

Figure 21:
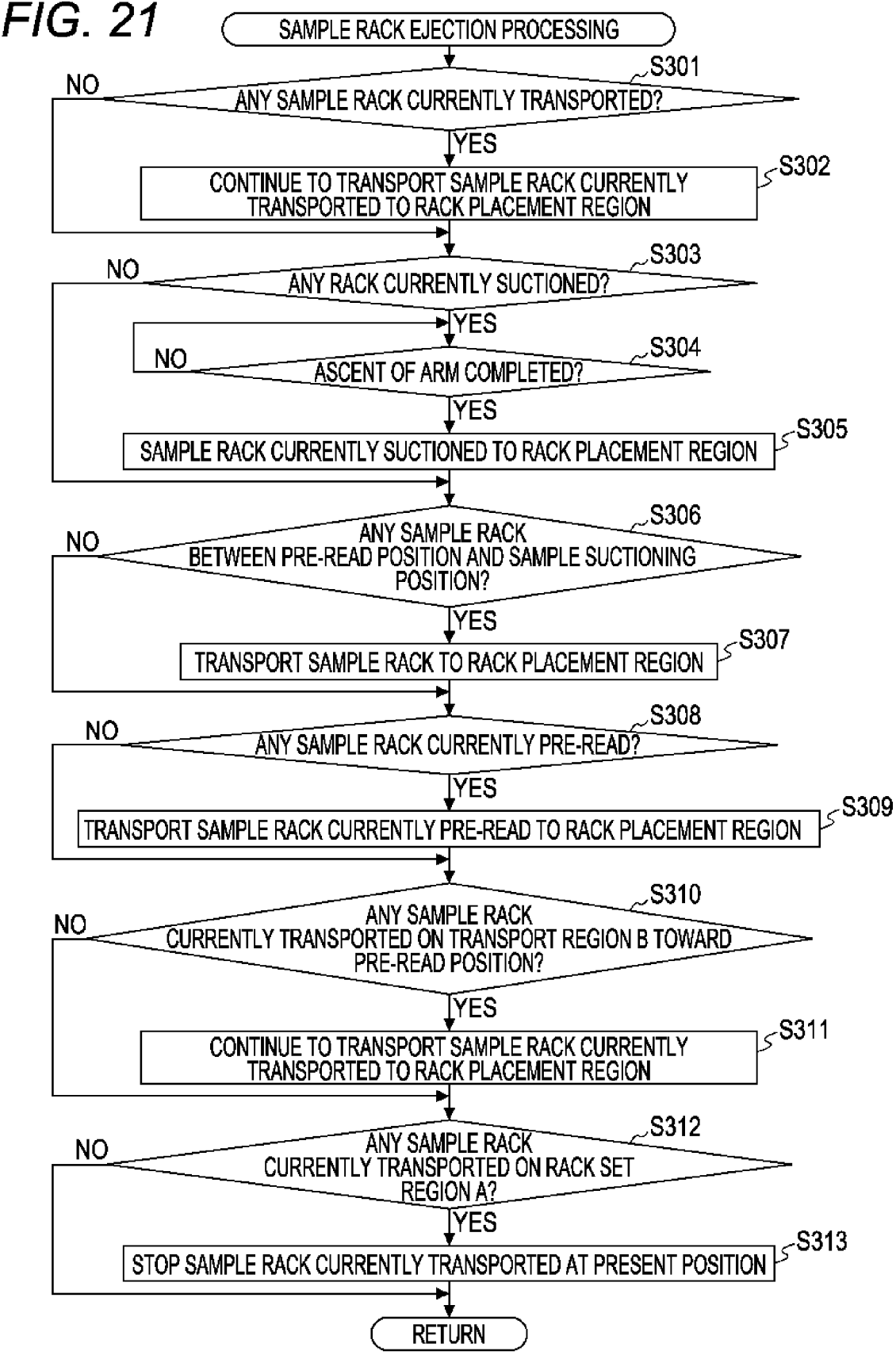
FIG. 21 is a flowchart illustrating a sample rack ejection processing according to the embodiment.

FIG. 21 is a flowchart illustrating steps of the "sample rack ejection processing" in the ejection processing illustrated in FIG. 19B.

In S301, it is determined whether there is any sample rack L currently transported from the transport region B to the rack placement region C after the sample suctioning for their sample containers T is completed. When determined that such a sample rack L is present (S301: YES), the sample rack L is transported to the rack placement region C (S302). When determined that such a sample rack L is not present (S301: NO), the processing proceeds to S303.

In S303, it is determined whether there is any sample rack L whose sample is currently suctioned at the sample suctioning position 52 or 53. When determined that such a sample rack L is present (S303: YES), the arm of the sample dispensing unit 21 or 22 is ascended (S304). When the ascent of the arm of the sample dispensing unit 21 or 22 is completed (S304: YES), the sample rack L whose sample was suctioned is transported leftward (X-axis positive direction) along the transport region B to the rack placement region C (S305). When determined that no sample rack L whose sample is currently suctioned (S303: NO), the processing proceeds to S306.

In S306, it is determined whether there is any sample rack L positioned between the pre-read position and the sample suctioning position 52 or 53 after the pre-read is over. When determined that such a sample rack L is present (S306: YES), the sample rack L is transported leftward (X-axis positive direction) along the transport region B to the rack placement region C (S307). When determined that there is no sample rack between the pre-read position and the sample suctioning position 52 or 53 (S306: NO), the processing proceeds to S308.

In S308, it is determined whether there is any sample rack L currently pre-read. When determined that there is the sample rack L currently pre-read (S308: YES), the sample rack currently pre-read is transported leftward along the transport region B to the rack placement region C before the pre-read is over (S309). When determined that there is no sample rack L currently pre-read (S308: NO), the processing proceeds to S310.

In S310, it is determined whether there is any sample rack L currently transported on the transport region B toward the pre-read position. When determined that there is such a sample rack L (S310: YES), the sample rack L is immediately transported to the rack placement region C without the barcode read and sample suctioning (S311). When determined that there is no such a sample rack L (S310: NO), the processing proceeds to S312. By the time when the transport operation of the sample rack L starts toward the pre-read position after the sample rack L is transported from the rack set region A to the right end of the transport region B, it is determined as YES in S310.

In S312, it is determined whether there is any sample rack L currently transported on the rack set region A toward the right end of the transport region B. When determined that there is such a sample rack (S312: YES), the sample rack L is stopped at the position (S313), and the "sample rack ejection processing" ends. When determined that there is no such a sample rack L (S312: NO), the "sample rack ejection processing" ends.

The item of "state" of the job list illustrated in FIG. 15 currently showing "pending" is rendered blank for the sample container T whose sample was suctioned in all of the sample containers T retained in the sample rack L forcibly ejected by the processing described above. The item of "state" of the job list illustrated in FIG. 15 shows "error", and "mask" is written in the item of measurement result for the sample container T which was pre-read but forcibly ejected before its sample was suctioned.

Figure 22:
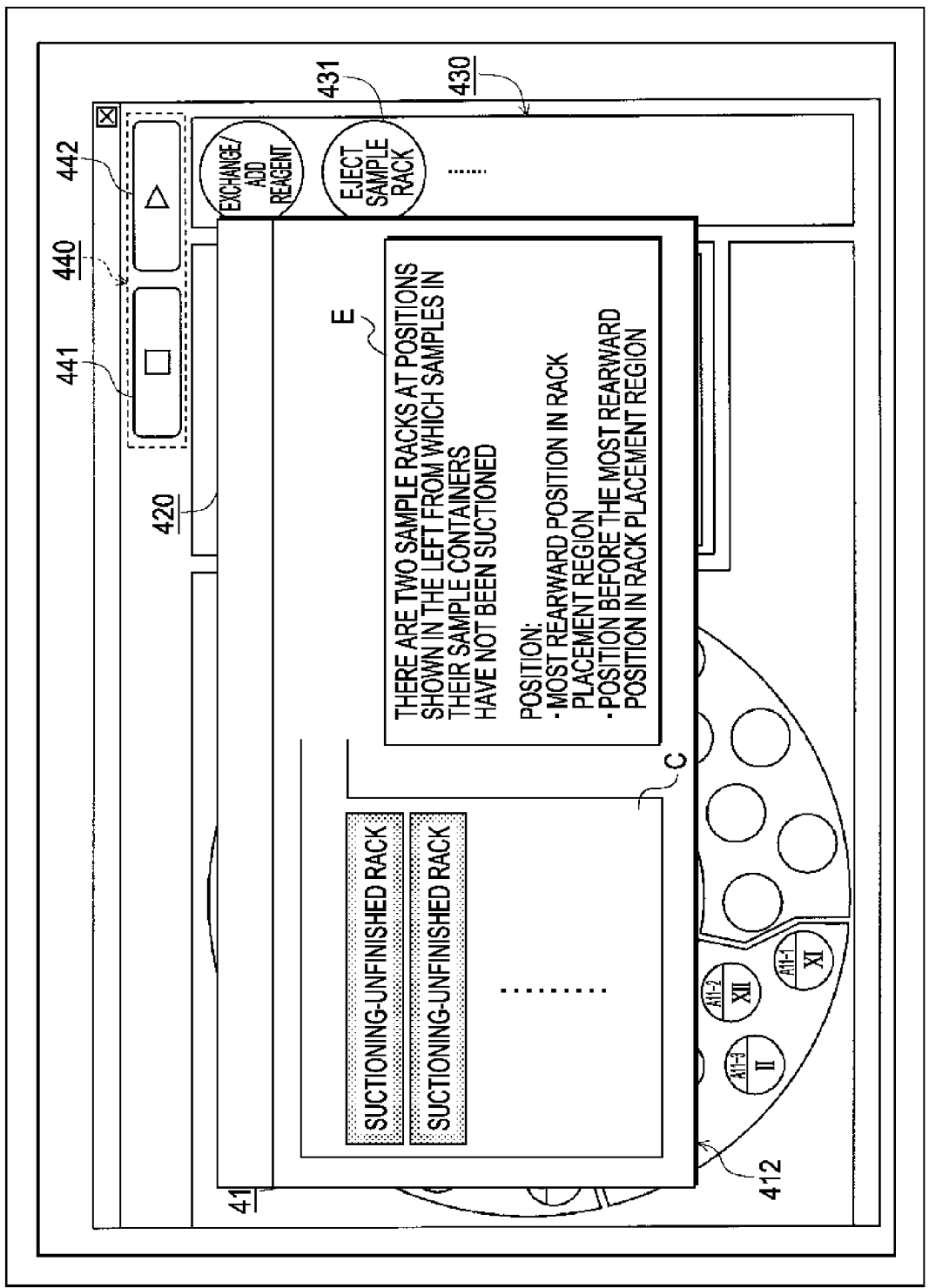
FIG. 22 illustrates a sample rack ejection screen according to the embodiment.

FIG. 22 illustrates an ejection screen for ejecting the sample rack L displayed on the display unit 320 of the information processing device 3.

The display screen is displayed when the OK button illustrated in FIG. 20 is pressed after the display illustrated in the figure is shown due to occurrence of the second suspension event. As illustrated in FIG. 22, the display screen displays an image illustration which indicates the position of the suctioning-unfinished rack on the rack placement region C and a descriptive message E which describes the position of the suctioning-unfinished rack. FIG. 22 illustrates a case in which two sample racks L are ejected by the ejection processing. The image illustration shows one suctioning-unfinished rack in the case where one sample rack L is ejected by the ejection processing, and the descriptive message E is changed to a message indicating that there is only one suctioning-unfinished rack. Whether it is one sample rack L or two sample racks L which were ejected by the ejection processing is determined based on the output from the rack transverse feed mechanism rotary encoder unit 222 and the output from the rack detector 235.

When the sample rack L is transported to the rack placement region C due to occurrence of the second suspension event, the operator, referring to the display screen, can distinguish the sample rack L in which the sample suctioning is still unfinished for some of the sample containers T from the sample rack L already transported to the rack placement region C after the sample suctioning is completed for all of its sample containers T, and can empirically know the current position of the suctioning-unfinished sample rack L. Further, the operator can readily know which of the sample racks L should be returned to the rack set region A to be measured again after the second suspension event has occurred.

Figure 19C:
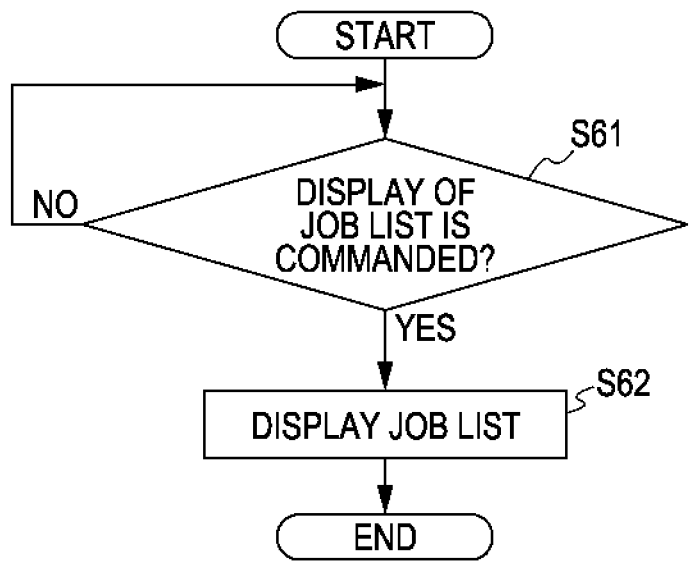

FIG. 19C is a flowchart illustrating steps of the job list display processing.

When the operator commands to display the job list via the information processing device 3 (S61: YES), a screen showing the job list is displayed on the display unit 320 of the information processing device 3 (see FIG. 16) (S32).

According to the present embodiment, as described above, the sample rack L is ejected into the rack placement region C by the "sample rack ejection processing" illustrated in FIG. 21 when the second suspension event occurs. Therefore, the operator can easily remove the sample rack L which was positioned in the transport region B from the rack placement region C even in the case where a part of the transport region B is covered with the front cover 55 as illustrated in FIG. 6.

Figure 23A:
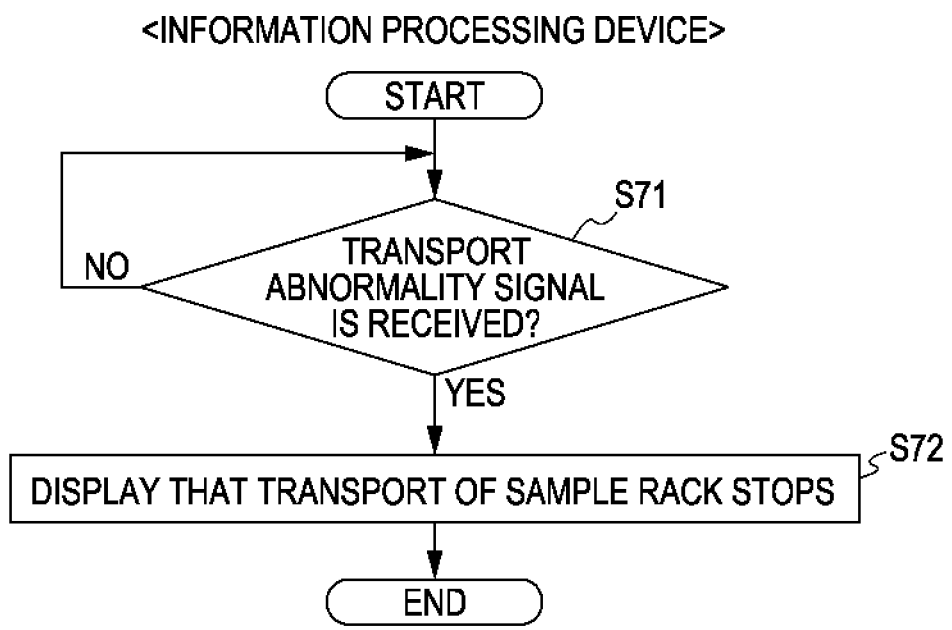
FIGS. 23A and 23B are flowcharts illustrating processing steps at the time of occurrence of a transport abnormality according to the embodiment.
Figure 23B:
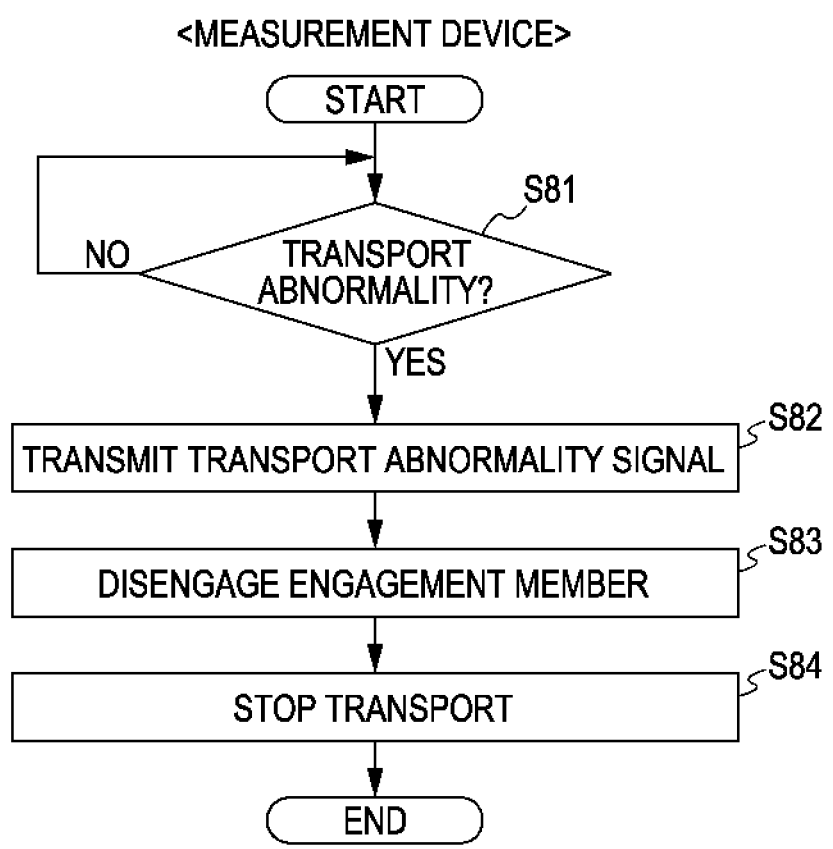

In the sample processing apparatus 1 according to the present embodiment, in the case where the abnormality is detected in the respective mechanisms of the measurement unit 10, the "sample rack ejection processing" is carried out, while in the case where the abnormality is detected in the transport unit 50, the sample rack L on the transport region B is not ejected into the rack placement region C but is stopped at a position thereof when the abnormality is detected. More specifically, referring to FIG. 23B, when the CPU 201 of the measurement device 2 determines that the operational abnormality has occurred in the rack transverse feed mechanism B2 based on the detection results of the rotary encoder B44 and the sensors B51 to 57 in the rack transverse feed mechanism B2 (S81: YES), the CPU 201 transmits a transport abnormality signal to the information processing device 3 (S82), and moves the engagement members B32 of the engagement unit B3 downward to disengage the engagement unit B3 from the sample rack L (S83). Then, the CPU 201 stops the transport operation of the sample rack L by the transport unit 50 (S84). Referring to FIG. 23A, when the CPU 301 of the information processing device 3 receives the transport abnormality signal from the measurement device 2 (S71), the CPU 301 makes the display unit 320 display thereon that the sample rack L was stopped due to the transport abnormality (S72).

Thus, according to the present embodiment, when the abnormality is detected in the transport unit 50, the sample rack L is not ejected but is stopped at the position when the abnormality is detected. Accordingly, the operator can confirm the position of the sample rack L when the abnormality has occurred in the transport unit 50 to thereby determine which of the mechanisms caused the abnormality. When the abnormality is detected in the transport unit 50, the engagement members B32 of the engagement unit B3 are moved downward. Therefore, the operator can remove the sample rack L from the transport region B by detaching the front cover 55. This technical advantage can prevent any malfunction of the apparatus caused by making the transport unit 50 to continue its transport operation even after the abnormality has occurred.

According to the present embodiment, the pipette of the sample dispensing unit 21, 22 is taken out of the sample container T when the second suspension event occurs during the sample suctioning, and the sample rack L is then transported to the rack placement region C. Therefore, the pipette of the sample dispensing unit 21, 22 can be prevented from contacting the sample container T and the sample rack L when the sample rack L is moved to the transport suspending position.

According to the present embodiment, when the second suspension event occurs during the pre-read operation, the sample rack L which is pre-read at the time is transported to the rack placement region C before the pre-read is finished. Thus, the sample rack L can be more speedily transported to the rack placement region C.

As illustrated in FIG. 10, the sample rack L is transported from the rack set region A to the transport region B after the measurement start signal is received by the information processing device 3. Therefore, even if the second suspension event occurs before the measurement start signal is received, the sample rack L stays at the position where it is stopped in the rack placement region A.

According to the present embodiment, the ejection screen illustrated in FIG. 22 is displayed when the sample rack L is transported to the rack placement region C due to occurrence of the second suspension event. By referring to this ejection screen, the sample rack L in which the sample suctioning is still unfinished in some of the sample containers T can be distinguished from the sample rack L transported to the rack placement region C after the samples in all of its sample containers T are suctioned, among the sample racks L positioned in the rack placement region C.

According to the present embodiment, the ejection screen illustrated in FIG. 22 displays the sample rack L forcibly ejected before the sample suctioning is completed. The job list screen illustrated in FIG. 16 may also display the sample rack L forcibly ejected before the sample suctioning is completed. When one sample rack L is forcibly ejected, the sample rack L is at the most rearward position in the rack placement region C. When two sample racks L are forcibly ejected, one of the sample racks L is at the most rearward position in the rack placement region C, and the other sample rack L is at a position before the most reward position. Therefore, when the field of the "rack number-position" of the sample rack L forcibly ejected by the most recent ejection processing is painted in red on the job list screen illustrated in FIG. 16, the operator can know the number of the ejected sample racks L, thereby knowing how many sample racks L from the most rearward position were ejected by the most recent ejection processing. However, in this case, when the sample rack L is forcibly ejected before its barcode is pre-read, this forcibly ejected sample rack L cannot be identified by the information processing device 3, and the forcible ejection of such a sample rack L is not displayed on the job list screen. In order to avoid such a problem, the sample rack L is not ejected to the rack placement region C but may be returned to the right-end position of the transport region B when the second suspension event has occurred before the barcode of the sample rack L is pre-read.

The embodiment of the present invention has been described above. The present invention, however, is not limited to the above embodiment, and the embodiment of the present invention can be variously modified.

According to the above embodiment, the sample processing apparatus 1 is a blood coagulation analyzing apparatus, however, the present invention is not limited thereto. Examples of the sample processing apparatus 1 may include, for example: immunoassay apparatus for measuring blood serums, a hemocyte counting apparatus for counting hemocytes in whole blood, a urine analyzing apparatus for measuring urine, and an analyzing apparatus for analyzing bone marrow fluid.

In the above embodiment, the measurement unit 10 for sample measurement is used as the sample processing unit. The sample processing unit may be a smear preparation unit for producing a smear by smearing a sample on a glass slide.

According to the present embodiment, the transport region B is covered with the front cover 55 to prevent any contact with the sample rack L on the transport region B, however, the present invention is not limited thereto. For example, a member having the shape of lattice may be provided in an upper area of the transport region B to prevent any possible contact with the sample rack L on the transport region B, and any member can be provided as far as it can prevent any contact with the sample rack L on the transport region B.

According to the above embodiment, at most two sample racks L can be simultaneously transported on the transport region B, however, the present invention is not limited thereto and at least three sample racks L may be simultaneously transported. In the case where the second suspension event occurs when at least three sample racks L are simultaneously transported, these sample racks L are appropriately ejected by the "sample rack ejection processing" illustrated in FIG. 21.

According to the above embodiment, as illustrated in FIG. 10, once the measuring operation starts, all of the samples in the sample containers T of the sample rack L are suctioned. However, the sample suctioning may be omitted for the sample containers T measured earlier.

Figure 24:
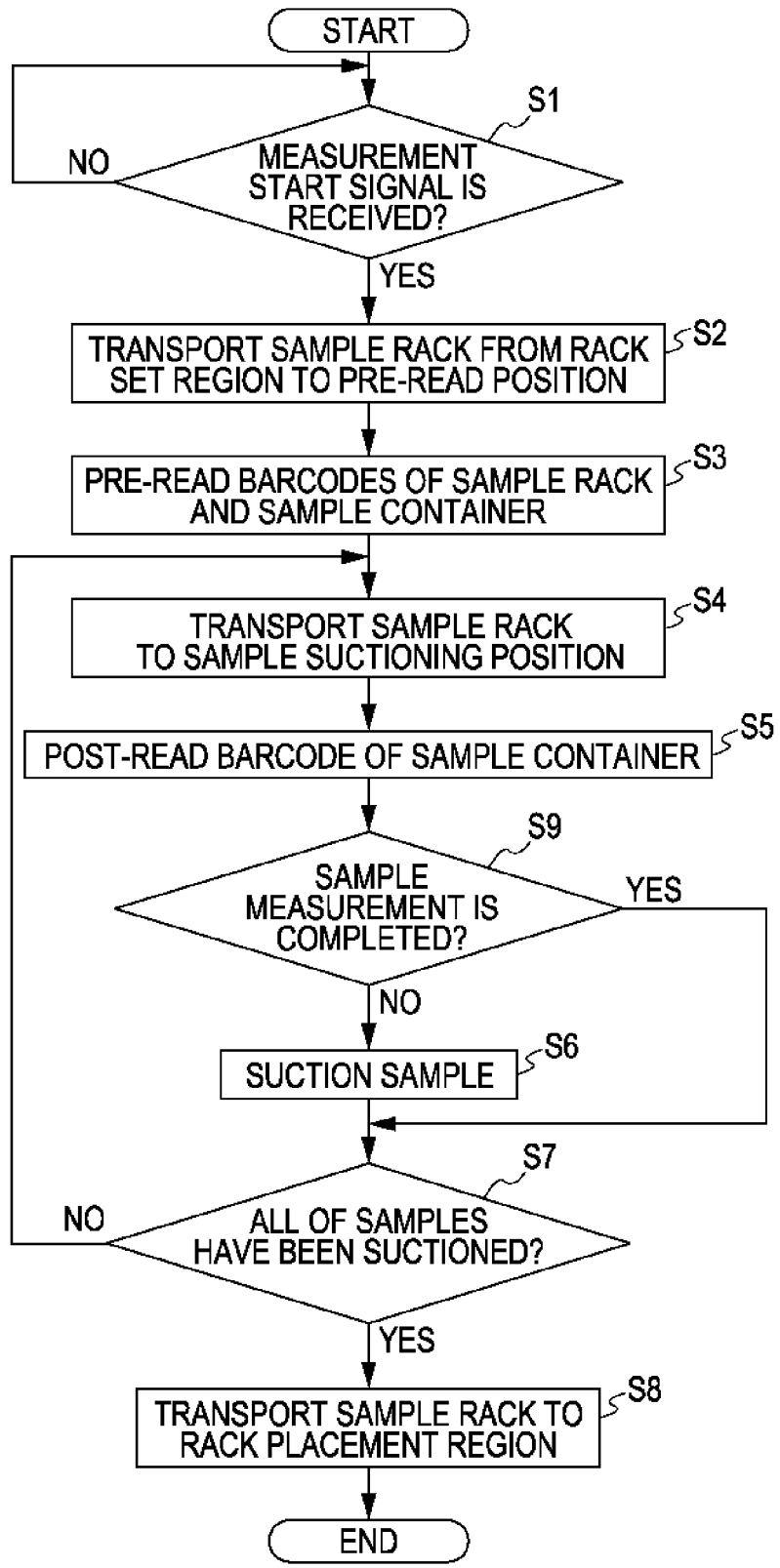
FIG. 24 is a modified example of a flowchart illustrating the sample suctioning processing according to the embodiment.

FIG. 24 is a flowchart illustrating steps of the sample suctioning processing in the example described above. To simplify the description, the same processing steps as those illustrated in FIG. 10 will not be described.

In S9, it is determined whether the measuring operation for the sample in the post-read sample container T is already completed. Whether or not the measuring operation is completed is determined by checking whether the item of "state" in the job list of FIG. 15 is blank. When it is determined that the sample measurement is not yet completed (S9: NO), the sample is suctioned (S6). When it is determined that the sample measurement is completed (S9: YES), the processing proceeds to S7.

As a result, when the sample rack L which holds some sample containers T for which the sample measurement is already completed is set in the rack set region A to start the measuring operation, for example, none of the samples is suctioned again from the sample containers T already measured. Thus, the measuring operation can be efficiently carried out.

According to the above embodiment, when the second suspension event occurs, the sample rack L on the transport region B is transported to the rack placement region C where the sample rack L can be removed from the transport unit 50. However, as long as the sample rack L is transported to the region where the sample rack L can be removed from the transport unit 50, the sample rack L may be transported from the transport region B to the rack set region A. In this case, a rack feed mechanism is provided, wherein the rack feed mechanism moves the sample rack L positioned at the right end of the transport region B (end in the X-axis negative direction) in the Y-axis negative direction. When the second suspension event occurs, the sample rack L near the center of the transport region B (area covered with the roof 54 and the front cover 55) may be transported to the transport region B not covered with the front cover 55 where the sample rack L can be removed (right-end and left-end positions of the transport region B).

According to the above embodiment, the sample rack L is transported to the rack placement region C in the case where the second suspension event occurs by the time when the transport of the sample rack L toward the pre-read position starts after the sample rack L is transported from the rack set region A to the right end of the transport region B. In this case, however, instead of transporting the sample rack L to the rack placement region C, the sample rack L may be stopped at the right end of the transport region B. Accordingly, it is unnecessary to return the sample rack L to the rack set region A after the second suspension event is resolved, which reduces the number of processing steps carried out by the operator.

According to the above embodiment, when the second suspension event occurs, the sample rack L is transported to the rack placement region C. In addition, the sample rack L may be similarly transported to the rack placement region C when the first suspension event occurs.

The automatic ejection condition due to the second suspension event is not limited to the examples described above. Other than the above-described examples, the condition may be associated with operation-related abnormality generated in the mechanisms.

According to the above embodiment, the CPU 201 of the measurement device 2 determines the operational abnormality in the mechanisms of the measurement unit 10 and the transport unit 50, however, the present invention is not limited thereto. The CPU 301 of the information processing device 3 or any other CPU may determine the operational abnormality.

The embodiment of the present invention can be variously modified within the scope of the technical idea disclosed in the appended claims.

What is claimed is:

1. A sample processing apparatus, comprising:
a sample processing unit for obtaining a sample from a sample container and performing a predetermined process on the sample;
a processing operation detector for detecting an operation state of the sample processing unit;
a transport unit which includes a rack set region where a sample rack holding the sample container is placed by an operator, a transport region for transporting the sample rack placed in the rack set region to the sample processing unit, a rack removal region where the sample rack is accessible to the operator and the sample rack is received from the transport region and retained, and a restraining member for restraining contact by the operator with the sample rack on the transport region; and
a transport controller programmed to control the transport unit to transport the sample rack on the transport region to the rack removal region when the processing operation detector has detected an abnormality of the operation state of the sample processing unit during an operation of transporting the sample rack in the transport region.

2. The sample processing apparatus of claim 1, wherein
the restraining member includes a cover portion which covers at least a part of the transport region; and
an upper side of the rack removal region is open.

3. The sample processing apparatus of claim 2, wherein the cover portion is removably attached to the transport unit.

4. The sample processing apparatus of claim 2, wherein
the sample processing unit includes a pipette for suctioning the sample from the sample container held by the sample rack positioned on the transport region, and
the cover portion covers a sample suctioning position where the sample is suctioned by the pipette.

5. The sample processing apparatus of claim 1, wherein
the sample processing unit includes a pipette for suctioning the sample from the sample container held by the sample rack positioned on the transport region; and
the transport controller is programmed to control the transport unit to transport the sample rack on the transport region to the rack removal region after the pipette has been removed from the sample container, if the processing operation detector has detected the abnormality while the pipette is inserted in the sample container.

6. The sample processing apparatus of claim 1, wherein
the sample rack holds a plurality of sample containers;
the sample processing apparatus further comprises an identification information reader for reading respective identification information for each of the sample containers held by the sample rack on the transport region; and
the transport controller is programmed to control the transport unit to transport the sample rack on the transport region to the rack removal region before a read operation by the identification information reader is finished if the processing operation detector has detected the abnormality during the read operation by the identification information reader.

7. The sample processing apparatus of claim 1, wherein
the transport region includes a transport path for transporting the sample rack received from the rack set region to the sample processing unit; and
the transport controller is programmed to control the transport unit to stop a transport of the sample rack in the rack set region if an abnormality is detected in the transport unit while the sample rack is positioned in the rack set region.

8. The sample processing apparatus of claim 1, wherein
the transport region is configured to receive a plurality of sample racks thereon; and
the transport controller is programmed to control the transport unit to transport the plurality of sample racks on the transport region to the rack removal region when the processing operation detector has detected the abnormality.

9. The sample processing apparatus of claim 1, further comprising
a notifying unit for generating a notification that the sample rack on the transport region has been transported to the rack removal region.

10. The sample processing apparatus of claim 1, wherein
the sample rack holds a plurality of sample containers; and
the rack removal region is a region where a specific sample rack, from which samples have been obtained by the sample processing unit from all of the sample containers held by the specific sample rack, is received from the transport region and retained.

11. The sample processing apparatus of claim 10, further comprising:
a display; and
a display controller programmed to show a screen on the display such that a specific sample rack, from which samples have been obtained by the sample processing unit from all of the sample containers held by the specific sample rack, is distinguished from a different sample rack already transported to the rack removal region before the processing operation detector has detected the abnormality.

12. The sample processing apparatus of claim 1, further comprising
a transport operation detector for detecting an operation state of the transport unit, wherein
the transport controller is programmed to control the transport unit to stop transport of the sample rack on the transport region when the transport operation detector has detected an abnormality of the operation state of the transport unit.

13. The sample processing apparatus of claim 1, further comprising
an input device for inputting a command to transport the sample rack on the transport region to the rack removal region, wherein
the transport controller is programmed to control the transport unit to transport the sample rack on the transport region to the rack removal region when the command has been inputted by the input device.

14. The sample processing apparatus of claim 1, wherein
the sample rack holds a first sample container and a second sample container; and
the transport controller is programmed to control the sample processing unit to obtain a sample from the second sample container when an operation by the sample processing unit is restarted, if the processing operation detector has detected the abnormality when the sample processing unit has finished obtaining a sample from the first sample container and has not finished obtaining the sample from the second sample container.

15. A sample processing apparatus, comprising:
a sample processing unit for obtaining a sample from a sample container and performing a predetermined process on the sample;
a processing operation detector for detecting an operation state of the sample processing unit;
a transport unit which includes a rack set region where a sample rack holding the sample container is placed by an operator, a transport region for transporting the sample rack placed in the rack set region to the sample processing unit, a rack removal region where the sample rack is accessible to the operator and the sample rack is received from the transport region and retained, and a restraining member for restraining contact by the operator with the sample rack on the transport region;
a transport operation detector for detecting an operation state of the transport unit; and
a transport controller programmed to control the transport unit to transport the sample rack to the rack removal region when the processing operation detector has detected an abnormality of the operation state of the sample processing unit during an operation of transporting the sample rack in the transport region, and programmed to control the transport unit to stop transport of the sample rack when the transport operation detector has detected an abnormality of the operation state of the transport unit during the operation of transporting the sample rack.

16. A sample processing apparatus, comprising:
a transport unit configured to transport a plurality of samples in racks holding sample containers to a sample processing unit in a transport region, and configured to transport the racks from a rack set region where the racks holding the sample containers are placed by an operator to a rack removal region where at least the sample containers are accessible to the operator;
a restraining member configured to prevent the operator from contacting at least the sample containers in at least a portion of the transport region; and
a processor and a memory programmed to perform instructions comprising: electronically controlling the transport unit to transport at least one of the racks in the transport region to the rack removal region in response to a signal indicating an abnormality of an operation of the sample processing unit during an operation of transporting the sample rack in the transport region.

* * * * *